(12) United States Patent
Schulman et al.

(10) Patent No.: US 7,114,502 B2
(45) Date of Patent: *Oct. 3, 2006

(54) BATTERY-POWERED PATIENT IMPLANTABLE DEVICE

(75) Inventors: Joseph H. Schulman, Santa Clarita, CA (US); Robert Dan Dell, Valencia, CA (US); John C. Gord, Venice, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 464 days.

This patent is subject to a terminal disclaimer.

(21) Appl. No.: 10/719,715

(22) Filed: Nov. 21, 2003

(65) Prior Publication Data

US 2004/0103906 A1 Jun. 3, 2004

Related U.S. Application Data

(60) Continuation-in-part of application No. 10/391,424, filed on Mar. 17, 2003, which is a division of application No. 09/677,384, filed on Sep. 30, 2000, now Pat. No. 6,564,807, which is a division of application No. 09/048,827, filed on Mar. 25, 1998, now Pat. No. 6,164,284, and a continuation-in-part of application No. 09/030,106, filed on Feb. 25, 1998, now Pat. No. 6,185,452, application No. 10/719,715.

(60) Provisional application No. 60/448,414, filed on Feb. 19, 2003, provisional application No. 60/042,447, filed on Mar. 27, 1997, provisional application No. 60/039,164, filed on Feb. 26, 1997.

(51) Int. Cl.
*A61B 19/00* (2006.01)

(52) U.S. Cl. .................................................. 128/899

(58) Field of Classification Search ........ 128/897–899, 128/903, 904; 600/300, 301; 607/2, 9, 17, 607/27, 30–32, 37–65
See application file for complete search history.

(56) References Cited

U.S. PATENT DOCUMENTS

| | | | |
|---|---|---|---|
| 4,041,954 | A | 8/1977 | Ohara |
| 4,146,029 | A | 3/1979 | Ellenwood, Jr. |
| 4,360,019 | A | 11/1982 | Portner et al. |
| 4,414,979 | A | 11/1983 | Hirshorn et al. |

(Continued)

FOREIGN PATENT DOCUMENTS

DE 3932405 4/1991

(Continued)

*Primary Examiner*—John P. Lacyk
(74) *Attorney, Agent, or Firm*—Lee J. Mandell

(57) ABSTRACT

A device configured for implanting beneath a patient's skin for the purpose of tissue, e.g., nerve or muscle, stimulation and/or parameter monitoring and/or data communication. Devices in accordance with the invention are comprised of a sealed housing, typically having an axial dimension of less than 60 mm and a lateral dimension of less than 6 mm, having a non-circular, e.g., an oval or polygon shaped, cross-section containing a power source for powering electronic circuitry within including a controller, an address storage means, a data signal receiver and an input/output transducer. When used as a stimulator, such a device is useful in a wide variety of applications to stimulate nerves and associated neural pathways. Alternatively, devices of the present invention are configurable to monitor a biological parameter. Furthermore, a placement structure is shown for facilitating placement of the implantable device proximate to neural/muscular tissue.

47 Claims, 24 Drawing Sheets

U.S. PATENT DOCUMENTS

| | | |
|---|---|---|
| 4,543,955 A | 10/1985 | Schroeppel |
| 4,612,934 A | 9/1986 | Borkan |
| 4,619,653 A | 10/1986 | Fischell |
| 4,714,462 A | 12/1987 | DiDomenico |
| 4,886,064 A | 12/1989 | Strandberg |
| 4,925,443 A | 5/1990 | Heilman et al. |
| 5,113,859 A | 5/1992 | Funke |
| 5,113,869 A | 5/1992 | Nappholz et al. |
| 5,167,625 A | 12/1992 | Jacobsen et al. |
| 5,170,801 A | 12/1992 | Casper et al. |
| 5,193,539 A | 3/1993 | Schulman et al. |
| 5,193,540 A | 3/1993 | Schulman et al. |
| 5,279,607 A | 1/1994 | Schentag et al. |
| 5,312,439 A | 5/1994 | Loeb |
| 5,312,446 A | 5/1994 | Holschbach et al. |
| 5,318,593 A | 6/1994 | Duggan |
| 5,324,316 A | 6/1994 | Schulman et al. |
| 5,358,514 A | 10/1994 | Schulman et al. |
| 5,397,350 A | 3/1995 | Chow et al. |
| 5,405,367 A | 4/1995 | Schulman et al. |
| 5,411,535 A | 5/1995 | Fujii et al. |
| 5,443,486 A | 8/1995 | Hrdlicka et al. |
| 5,481,262 A | 1/1996 | Urbas et al. |
| 5,507,737 A | 4/1996 | Palmskog |
| 5,544,651 A | 8/1996 | Wilk |
| 5,558,640 A | 9/1996 | Pfeiler et al. |
| 5,562,713 A | 10/1996 | Silvian |
| 5,571,148 A | 11/1996 | Loeb et al. |
| 5,591,217 A | 1/1997 | Barreras |
| 5,694,952 A | 12/1997 | Lidman et al. |
| 5,725,559 A | 3/1998 | Alt et al. |
| 5,728,154 A | 3/1998 | Crossett et al. |
| 5,733,313 A | 3/1998 | Barreras, Sr. et al. |
| 5,759,199 A | 6/1998 | Snell et al. |
| 5,766,231 A | 6/1998 | Erickson et al. |
| 5,782,799 A | 7/1998 | Jacobson et al. |
| 5,807,397 A | 9/1998 | Barreras |
| 5,810,735 A | 9/1998 | Halperin et al. |
| 6,051,017 A | 4/2000 | Loeb et al. |
| 6,061,596 A | 5/2000 | Richmond et al. |
| 6,122,546 A | 9/2000 | Sholder et al. |
| 6,164,284 A | 12/2000 | Schulman et al. |
| 6,185,452 B1 | 2/2001 | Schulman et al. |
| 6,208,894 B1 | 3/2001 | Schulman et al. |
| 6,315,721 B1 | 11/2001 | Schulman et al. |
| 6,564,807 B1 * | 5/2003 | Schulman et al. .......... 128/899 |
| 6,733,485 B1 | 5/2004 | Whitehurst et al. |
| 2004/0059392 A1 | 3/2004 | Parramon et al. |

FOREIGN PATENT DOCUMENTS

| | | |
|---|---|---|
| EP | 0561068 A2 | 9/1993 |

* cited by examiner

OPEN LOOP CONTROL/MONITOR

OPTIONAL USE OF
TRANSLATION TABLE

CLOSED LOOP CONTROL

EXEMPLARY INJURY

COORDINATED CLOSED LOOP HAND CONTROL

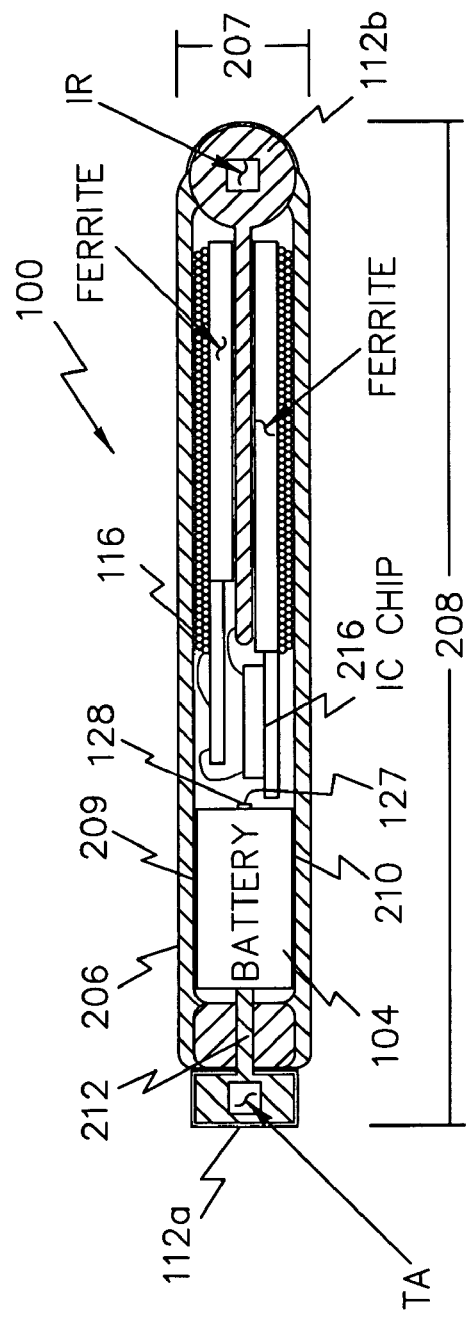
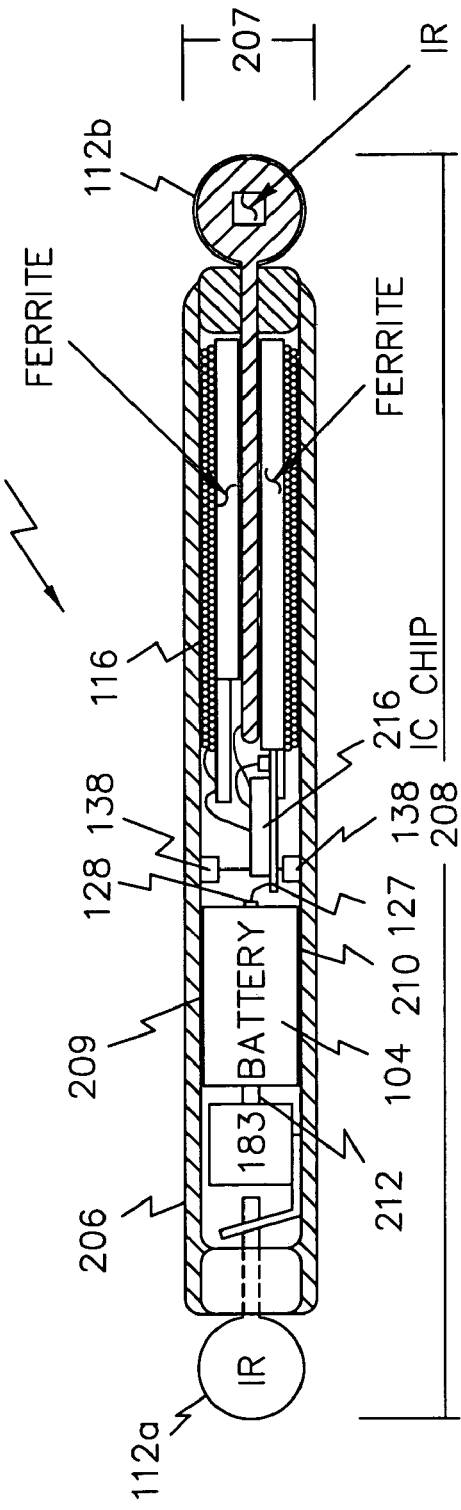
FIG. 10A
FIG. 10B

BATTERY-POWERED PATIENT IMPLANTABLE DEVICE

This application is a continuation-in-part of U.S. patent application Ser. No. 10/391,424, filed Mar. 17, 2003. U.S. patent application Ser. No. 10/391,424 is a divisional of U.S. patent application Ser. No. 09/677,384, filed Sep. 30, 2000, now U.S. Pat. No. 6,564,807. U.S. Pat. No. 6,564,807 is a divisional of U.S. patent application Ser. No. 09/048,827, filed Mar. 25, 1998, now U.S. Pat. No. 6,164,284. U.S. Pat. No. 6,164,284 is a continuation-in-part of U.S. patent application Ser. No. 09/030,106, filed Feb. 25, 1998, now U.S. Pat. No. 6,185,452 and claims the benefit of U.S. Provisional Application No. 60/042,447, filed Mar. 27, 1997. U.S. Pat. No. 6,185,452 claims the benefit of U.S. Provisional Application No. 60/039,164, filed Feb. 26, 1997. Additionally, the present application claims the benefit of U.S. Provisional Application No. 60/448,414, filed Feb. 19, 2003.

BACKGROUND OF THE INVENTION

The present invention relates to systems for monitoring and/or affecting parameters of a patient's body for the purpose of medical diagnosis and/or treatment. More particularly, systems in accordance with the invention are characterized by a plurality of devices, preferably battery-powered, configured for implanting within a patient's body, each device being configured to sense a body parameter, e.g., temperature, $O_2$ content, physical position, etc., and/or to affect a parameter, e.g., via nerve stimulation.

Applicants' great great grandparent U.S. patent application Ser. No. 09/030,106 entitled "Battery Powered Patient Implantable Device", incorporated herein by reference, describes devices configured for implantation within a patient's body, i.e., beneath a patient's skin, for performing various functions including: (1) stimulation of body tissue, (2) sensing of body parameters, and (3) communicating between implanted devices and devices external to a patient's body.

SUMMARY OF TH INVENTION

The present invention is directed to a system for monitoring and/or affecting parameters of a patient's body and more particularly to such a system comprised of a system control unit (SCU) and one or more devices implanted in the patient's body, i.e., within the envelope defined by the patient's skin. Each said implanted device is configured to be monitored and/or controlled by the SCU via a wireless communication channel.

In accordance with the invention, the SCU comprises a programmable unit capable of (1) transmitting commands to at least some of a plurality of implanted devices and (2) receiving data signals from at least some of those implanted devices. In accordance with a preferred embodiment, the system operates in a closed loop fashion whereby the commands transmitted by the SCU are dependent, in part, on the content of the data signals received by the SCU.

In accordance with a preferred embodiment, each implanted device is configured similarly to the devices described in Applicants' great great grandparent U.S. patent application Ser. No. 09/030,106 and typically comprises a sealed housing suitable for injection into the patient's body. Each housing preferably contains a power source having a capacity of at least 1 microwatt-hour, preferably a rechargeable battery, and power consuming circuitry preferably including a data signal transmitter and receiver and sensor/stimulator circuitry for driving an input/output transducer.

In accordance with a significant aspect of the preferred embodiment, a preferred SCU is also implemented as a device capable of being injected into the patient's body. Wireless communication between the SCU and the other implanted devices can be implemented in various ways, e.g., via a modulated sound signal, AC magnetic field, RF signal, or electrical conduction.

In accordance with a further aspect of the invention, the SCU is remotely programmable, e.g., via wireless means, to interact with the implanted devices according to a treatment regimen. In accordance with a preferred embodiment, the SCU is preferably powered via an internal power source, e.g., a rechargeable battery. Accordingly, an SCU combined with one or more battery-powered implantable devices, such as those described in the great great grandparent application, form a self-sufficient system for treating a patient.

In accordance with a preferred embodiment, the SCU and other implanted devices are implemented substantially identically, being comprised of a sealed housing configured to be injected into the patient's body. Each housing contains sensor/stimulator circuitry for driving an input/output transducer, e.g., an electrode, to enable it to additionally operate as a sensor and/or stimulator.

Alternatively, the SCU could be implemented as an implantable but non-injectable housing which would permit it to be physically larger enabling it to accommodate larger, higher capacity components, e.g., a battery, microcontroller, etc. As a further alternative, the SCU could be implemented in a housing configured for carrying on the patient's body outside of the skin defined envelope, e.g., in a wrist band.

In accordance with the invention, the commands transmitted by the SCU can be used to remotely configure the operation of the other implanted devices and/or to interrogate the status of those devices. For example, various operating parameters, e.g., the pulse frequency, pulse width, trigger delays, etc., of each implanted device can be controlled or specified in one or more commands addressably transmitted to the device. Similarly, the sensitivity of the sensor circuitry and/or the interrogation of a sensed parameter, e.g., battery status, can be remotely specified by the SCU.

In accordance with a significant feature of the preferred embodiment, the SCU and/or each implantable device includes a programmable memory for storing a set of default parameters. In the event of power loss, SCU failure, or any other catastrophic occurrence, all devices default to the safe harbor default parameters. The default parameters can be programmed differently depending upon the condition being treated. In accordance with a further feature, the system includes a switch, preferably actuatable by an external DC magnetic field, for resetting the system to its default parameters.

In an exemplary use of a system in accordance with the present invention, a patient with nerve damage can have a damaged nerve "replaced" by an implanted SCU and one or more implanted sensors and stimulators, each of which contains its own internal power source. In this exemplary system, the SCU would monitor a first implanted sensor for a signal originating from the patient's brain and responsively transmit command signals to one or more stimulators implanted past the point of nerve damage. Furthermore, the SCU could monitor additional sensors to determine variations in body parameters and, in a closed loop manner, react to control the command signals to achieve the desired treatment regimen.

In a further aspect of a preferred embodiment of the present invention, a placement structure is shown for facilitating placement of an implantable device having at least two electrodes proximate to neural/muscular tissue, wherein the placement structure comprises (1) a holder having a hollow cavity formed within for holding and retaining the implantable device within; (2) at least one set of elastic wings for capturing neural/muscular tissue; and wherein the placement structure is primarily formed from a biocompatible plastic.

The novel features of the invention are set forth with particularity in the appended claims. The invention will be best understood from the following description when read in conjunction with the accompanying drawings.

BRIEF DESCRIPTION OF TH DRAWINGS

FIG. 1 is a simplified block diagram of the system of the present invention comprised of implanted devices, e.g., microstimulators, microsensors and microtransponders, under control of an implanted system control unit (SCU).

FIG. 2 comprises a block diagram of the system of FIG. 1 showing the functional elements that form the system control unit and implanted microstimulators, microsensors and microtransponders.

FIG. 3A comprises a block diagram of an exemplary implanted device, as shown in the great great grandparent application, including a battery for powering the device for a period of time in excess of one hour in response to a command from the system control unit.

FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 10A shows a side view of a battery-powered implanted device, e.g., a microstimulator, made in accordance with the present invention.

FIG. 10B shows a side view of another implantable battery-powered device, one employing an internal coupling capacitor, made in accordance with the invention.

FIG. 25 is a perspective view of an exemplary placement structure of the present invention which is formed for holding one of the aforementioned implantable device in close proximity to a nerve, muscle tissue, or the like.

Figure 25:
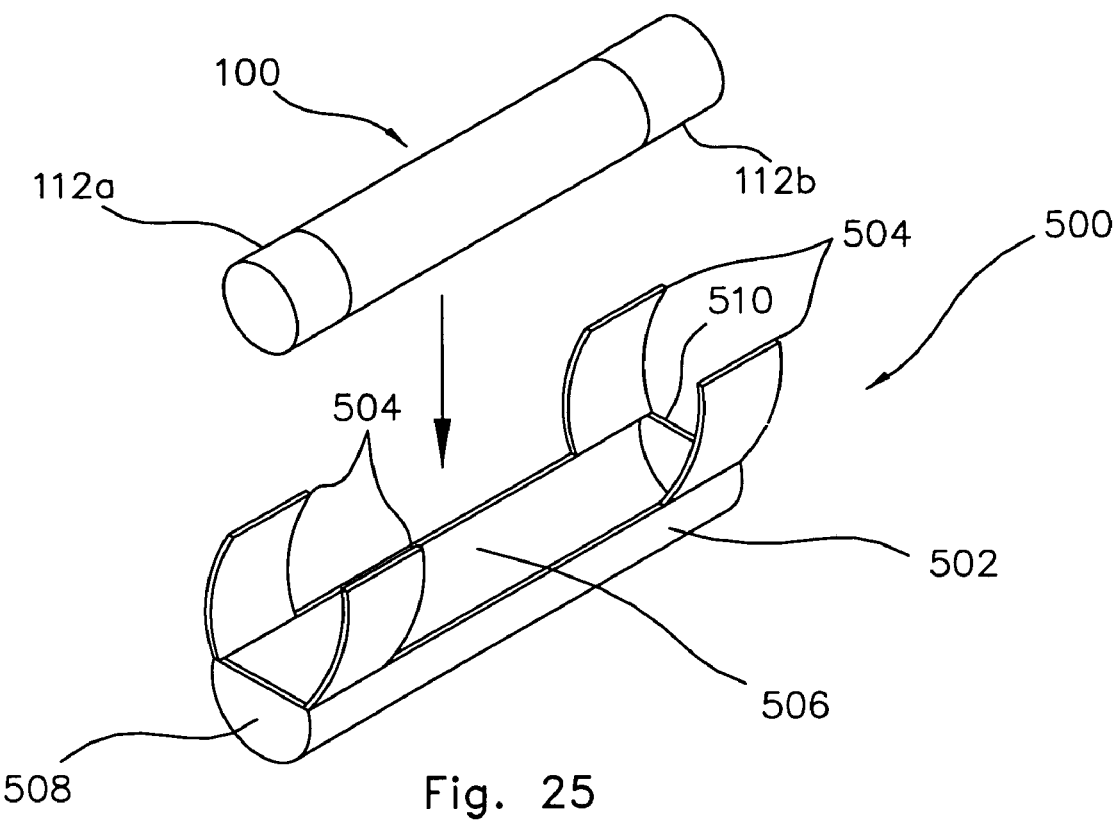
Figure 26:
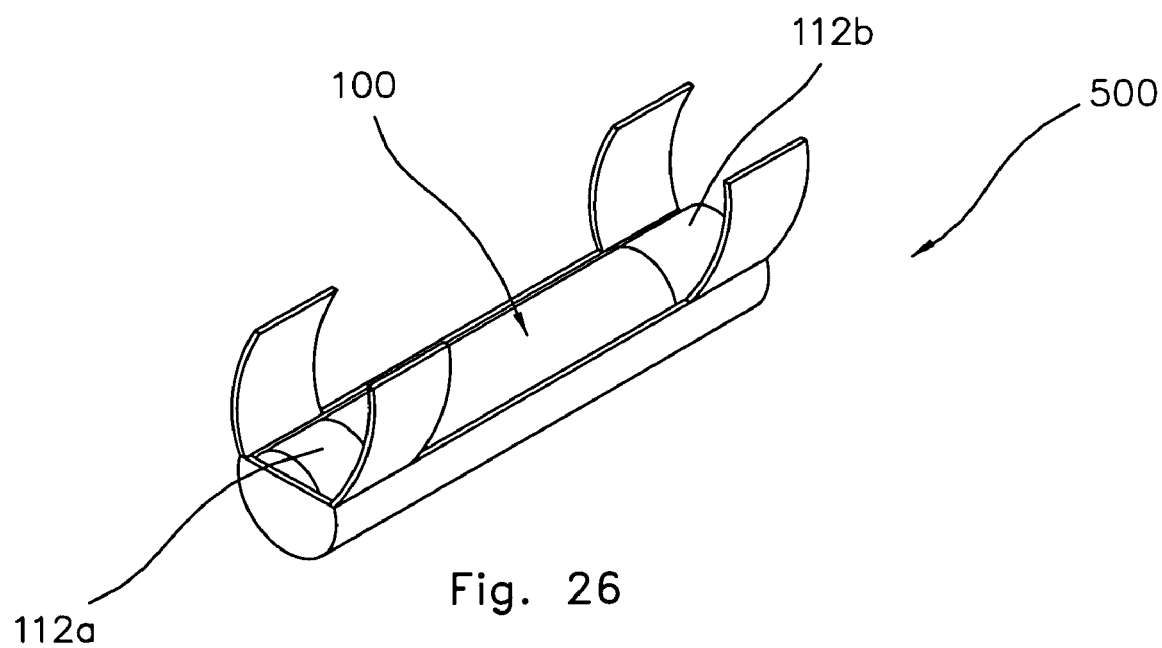
FIG. 26 is a perspective view of the placement structure of FIG. 25 having one of the aforementioned placement devices held within a hollow cavity within its holder portion.
Figure 35:
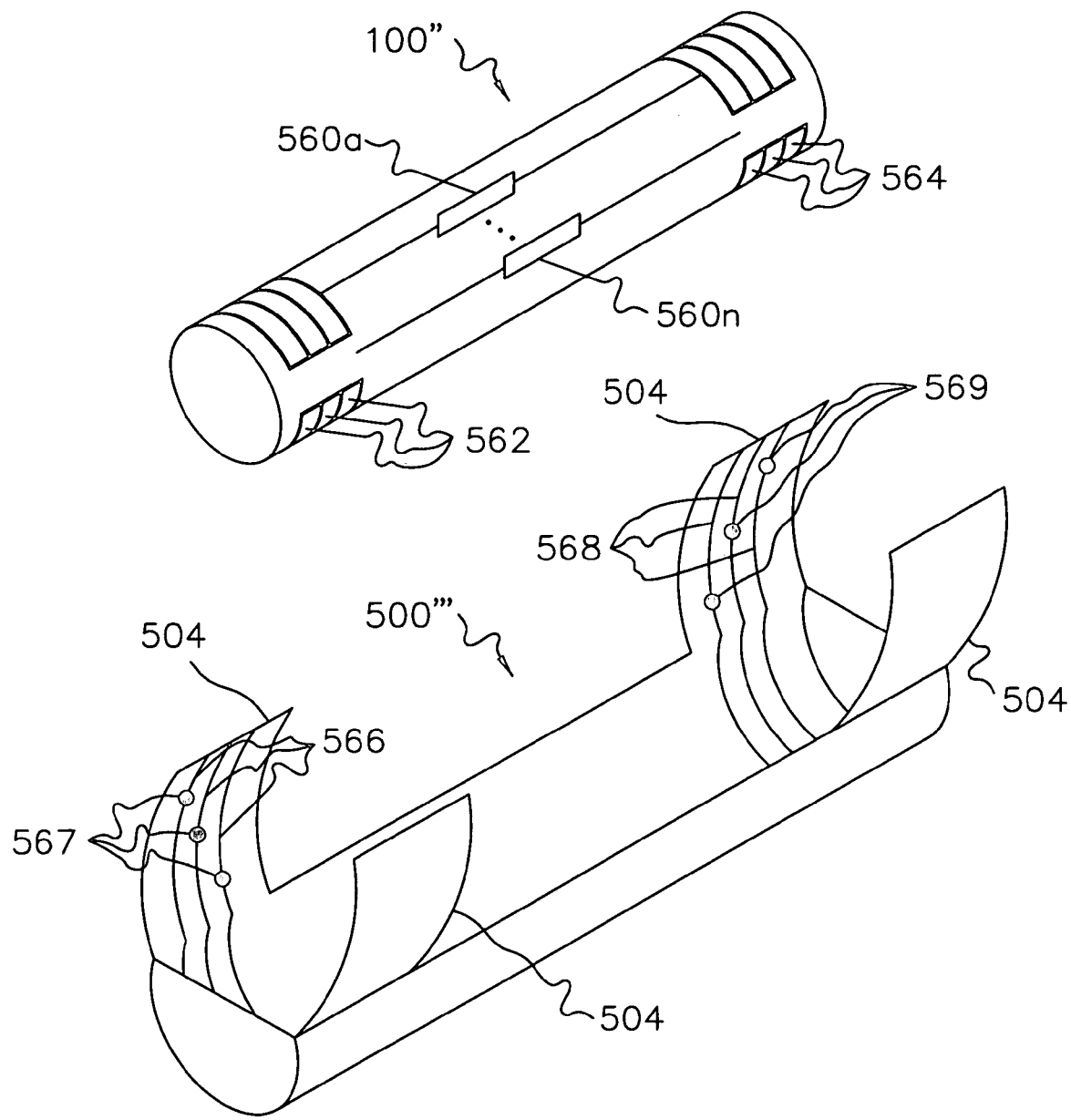

FIG. 35 is an alternative embodiment of the placement structure of FIG. 25 and the implantable medical device of FIGS. 10A–10D wherein the implantable medical device additionally includes a plurality of stimulator/sensor circuitry portions that are coupled via a plurality of electrode connectors and a plurality of conductive paths to inner portions of the wings and the cavity of the placement structure to provide stimulation to or sensing from displaced portions of the neural/muscular tissue.

Figure 36:
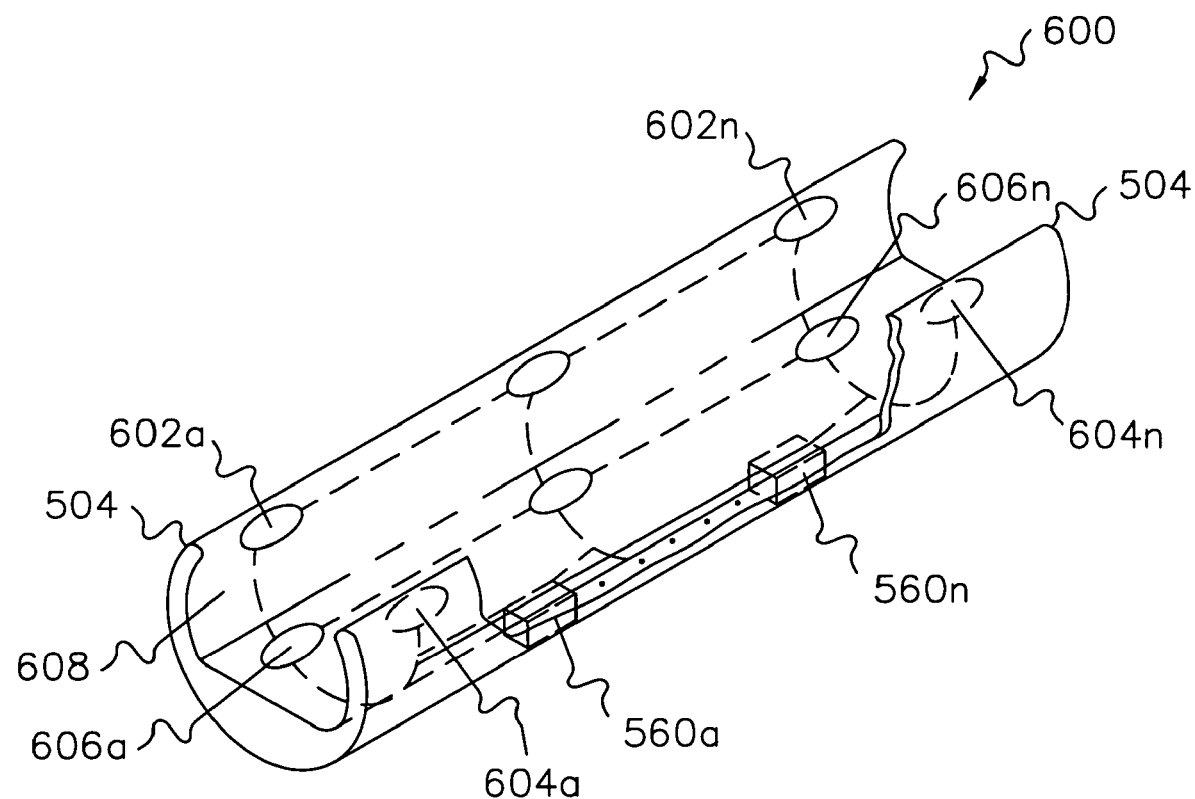

FIG. 36 shows an alternative implementation of that which is functionally described in relation to FIG. 35. However, in this implementation a single, essentially U-shaped structure having elastic wings is integrally formed which encompasses the functionality of the implantable medical device of FIGS. 10A–10D contained within the placement structure.

Figure 37:
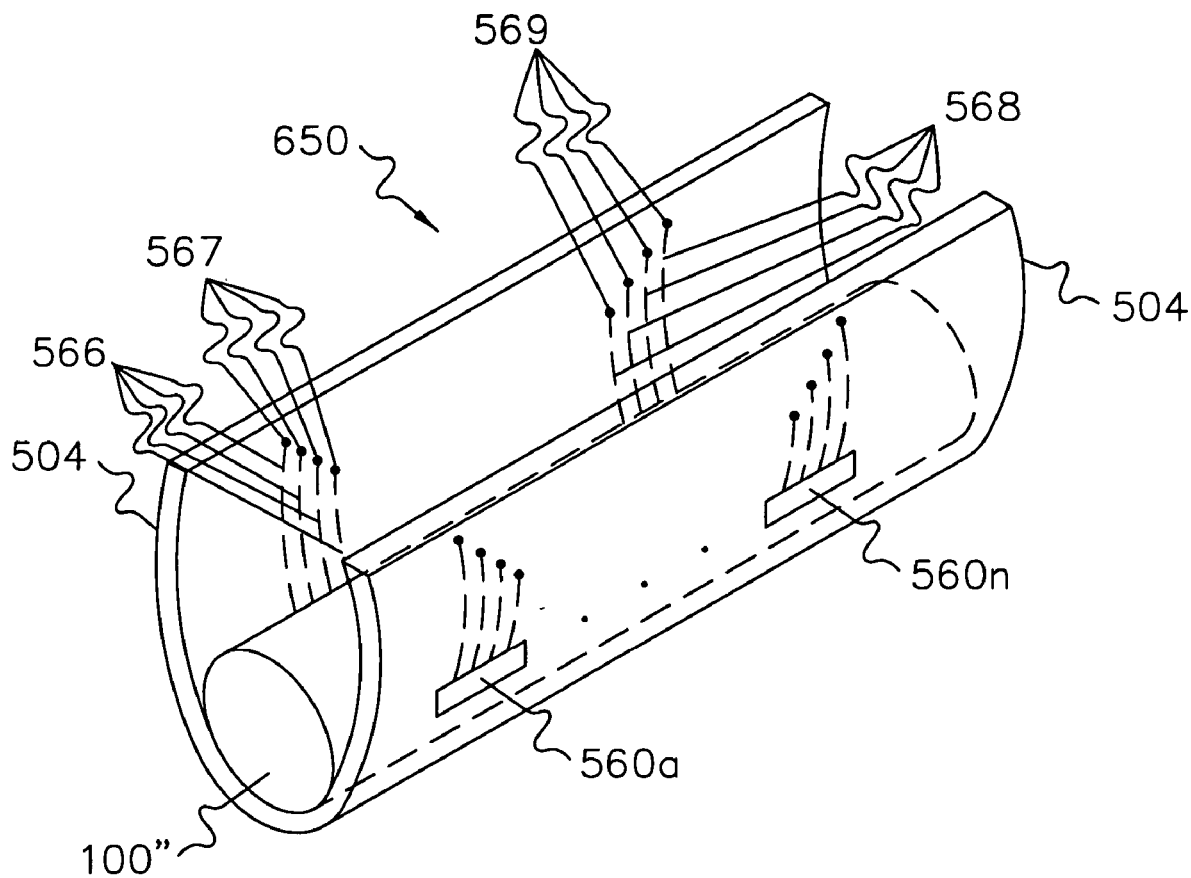

FIG. 37 shows a next alternative implementation of that which is functionally described in relation to FIGS. 35 and 36 to the extent that it too is an integral device but it has its elastic wings 504 formed from a silicon rubber impregnated cloth that is permanently attached to the functional equivalent of the implantable medical device which was described in reference to FIGS. 10A–10D.

D TAIL D DESCRIPTION OF TH PR FERRED EMBODIMENTS

The present invention is directed to a system for monitoring and/or affecting parameters of a patient's body and more particularly to such a system comprised of a system control unit (SCU) and one or more devices implanted in a patient's body, i.e., within the envelope defined by the patient's skin. Each such implantable device is configured to be monitored and/or controlled by the SCU via a wireless communication channel.

In accordance with the invention, the SCU comprises a programmable unit capable of (1) transmitting commands to at least some of a plurality of implanted devices and (2) receiving data signals from at least some of those implanted devices. In accordance with a preferred embodiment, the system operates in closed loop fashion whereby the commands transmitted by the SCU are dependent, in part, on the content of the data signals received by the SCU.

In accordance with a preferred embodiment, each implanted device is configured similarly to the devices described in Applicants' great great grandparent U.S. patent application Ser. No. 09/030,106 and typically comprises a sealed housing suitable for injection into the patient's body. Each housing preferably contains a power source having a capacity of at least 1 microwatt-hour, preferably a rechargeable battery, and power consuming circuitry preferably including a data signal transmitter and receiver and sensor/stimulator circuitry for driving an input/output transducer.

Figure 1:
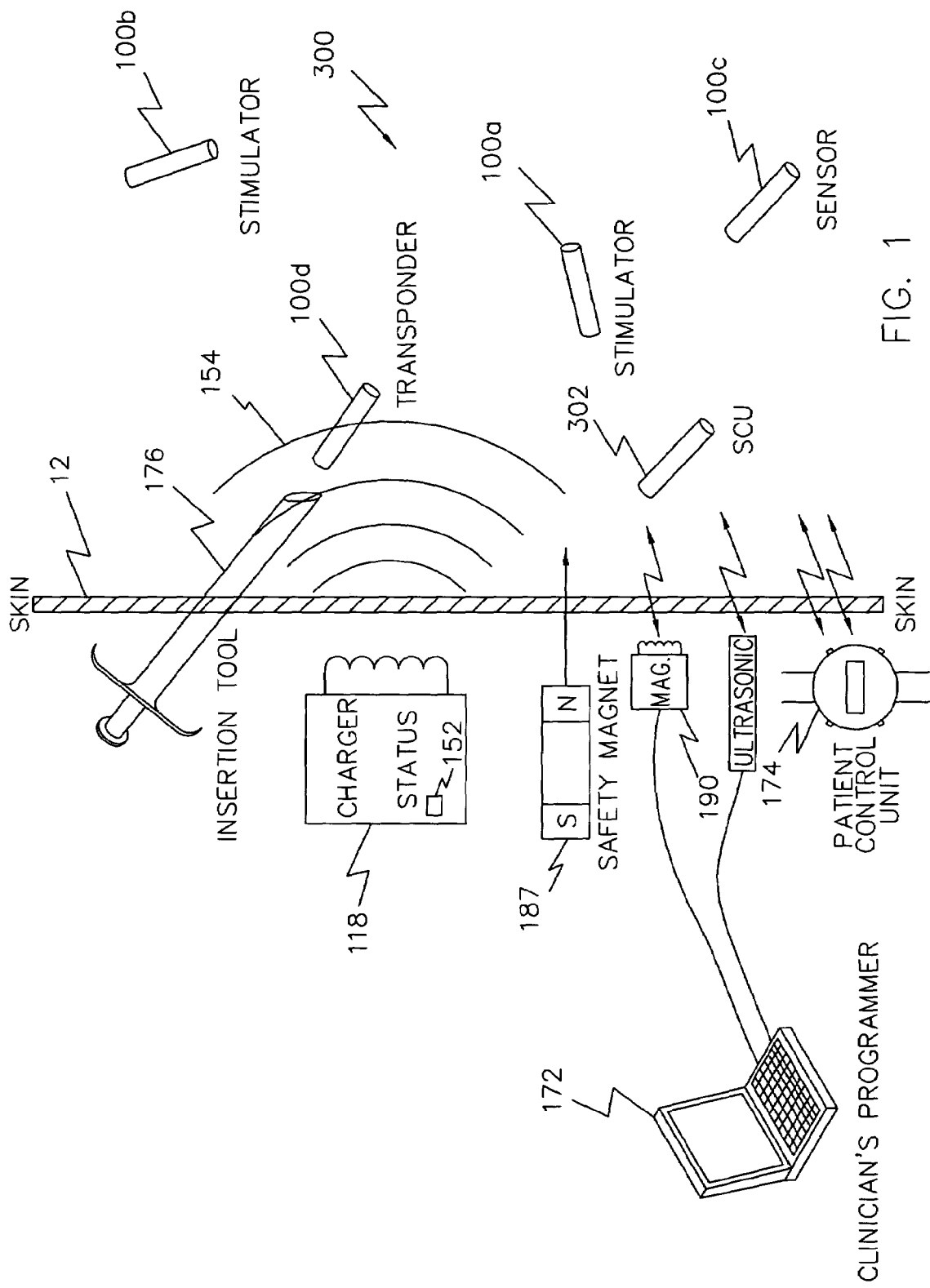
Figure 2:
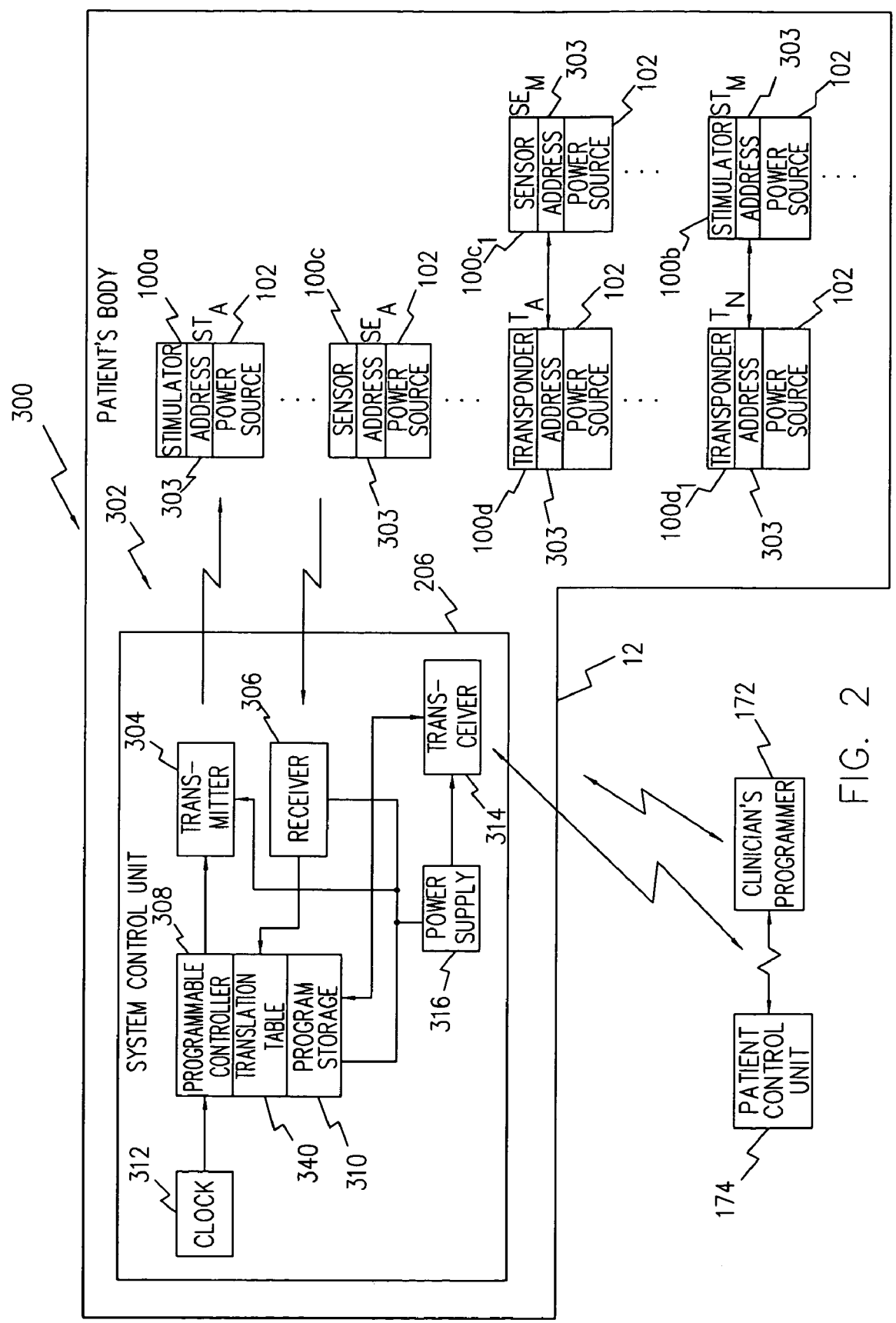

FIG. 1 (essentially corresponding to FIG. 2 of the great great grandparent application) and FIG. 2 show an exemplary system 300 made of implanted devices 100, preferably battery powered, under control of a system control unit (SCU) 302, preferably also implanted beneath a patient's skin 12. As described in the great great grandparent application, potential implanted devices 100 (see also the block diagram shown in FIG. 3A) include stimulators, e.g., 100a, sensors, e.g., 100c, and transponders, e.g., 100d. Such stimulators, e.g., 100a, can be remotely programmed to output a sequence of drive pulses to body tissue proximate to its implanted location via attached electrodes. The sensors, e.g., 100c, can be remotely programmed to sense one or more physiological or biological parameters in the implanted environment of the device, e.g., temperature, glucose level, $O_2$ content, etc. Transponders, e.g., 100d, are devices which can be used to extend the interbody communication range between stimulators and sensors and other devices, e.g., a clinician's programmer 172 and a patient control unit 174. Preferably, these stimulators, sensors and transponders are contained in sealed elongate housing having an axial dimension of less than 60 mm and a lateral dimension of less than 6 mm. Accordingly, such stimulators, sensors and transponders are respectively referred to as microstimulators, microsensors, and microtransponders. Such microstimulators and microsensors can thus be positioned beneath the skin within a patient's body using a hypodermic type insertion tool 176.

As described in the great great grandparent application, microstimulators and microsensors are remotely programmed and interrogated via a wireless communication channel, e.g., modulated AC magnetic, sound (i.e., ultrasonic), RF or electric fields, typically originating from control devices external to the patient's body, e.g., a clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with an identification code (ID) 303 specified in address storage circuitry 108 (see FIG. 3A) as described in the great great grandparent application.

By using one or more such implantable devices in conjunction with the SCU 302 of the present invention, the capabilities of such implanted devices can be further expanded. For example, in an open loop mode (described below in reference to FIG. 5), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 7–9), the SCU 302 periodically interrogates one or more microsensors and accordingly adjust the commands transmitted to one or more microstimulators.

FIG. 2 shows the system 300 of the present invention comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body as described in the great great grandparent application in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock 312, preferably a real time clock that permits tasks to be scheduled at specified times of day.

The signal transmitter 304 and signal receiver 306 preferably communicate with implanted devices 100 using sound means, i.e., mechanical vibrations, using a transducer having a carrier frequency modulated by a command data signal. In a preferred embodiment, a carrier frequency of 100 KHz is used which corresponds to a frequency that freely passes through a typical body's fluids and tissues. However, such sound means that operate at any frequency, e.g., greater than 1 Hz, are also considered to be within the scope of the present invention. Alternatively, the signal transmitter 304 and signal receiver 306 can communicate using modulated AC magnetic, RF, or electric fields.

The clinician's programmer 172 and/or the patient control unit 174 and/or other external control devices can also communicate with the implanted devices 100, as described in the great great grandparent application, preferably using a modulated AC magnetic field. Alternatively, such external devices can communicate with the SCU 302 via a transceiver 314 coupled to the programmable controller 308. Since, in a preferred operating mode, the signal transmitter 304 and signal receiver 306 operate using sound means, a separate transceiver 314 which operates using magnetic means is used for communication with external devices. However, a single transmitter 304/receiver 306 can be used in place of transceiver 314 if a common communication means is used.

Figure 3A:
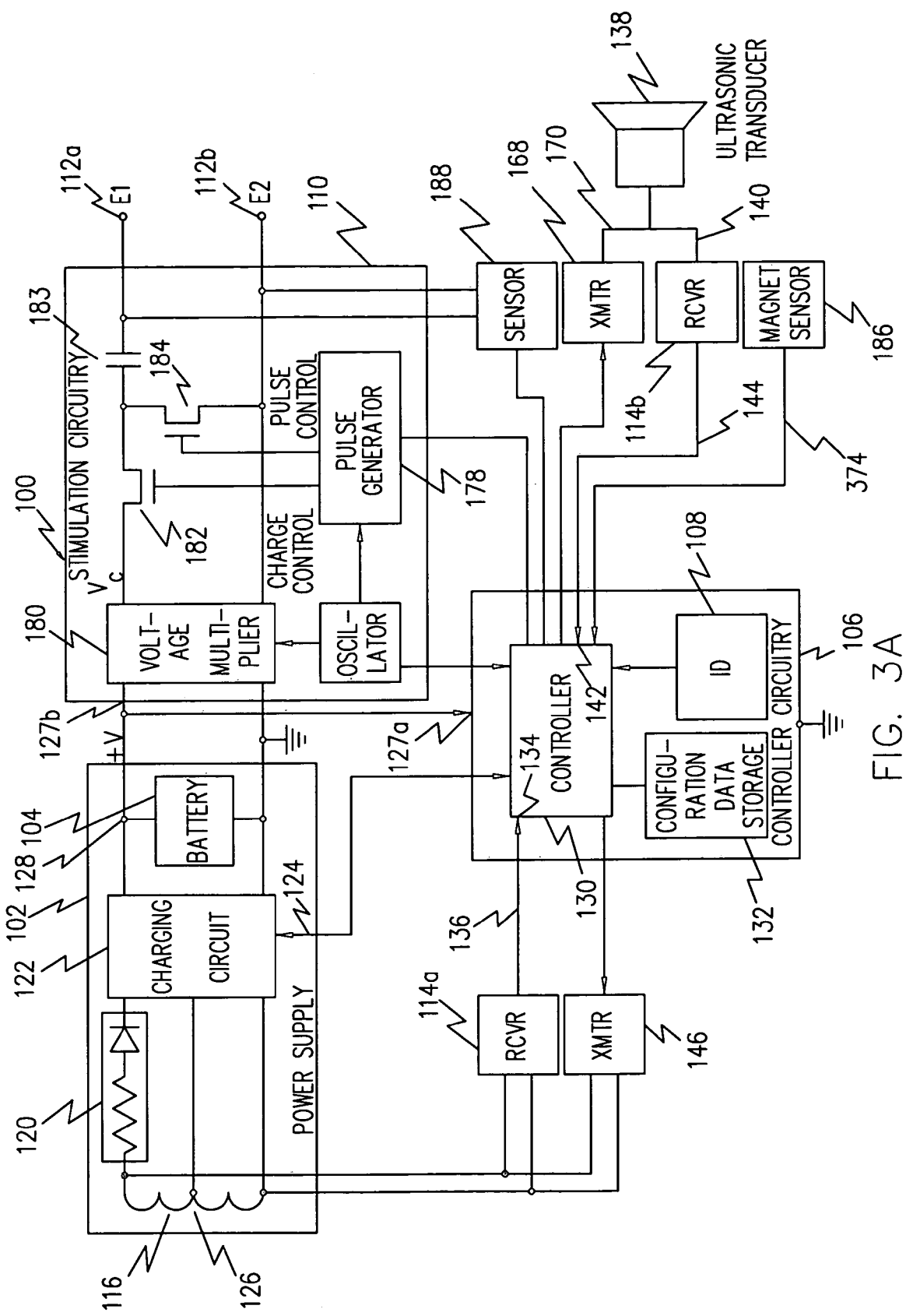
Figure 3B:
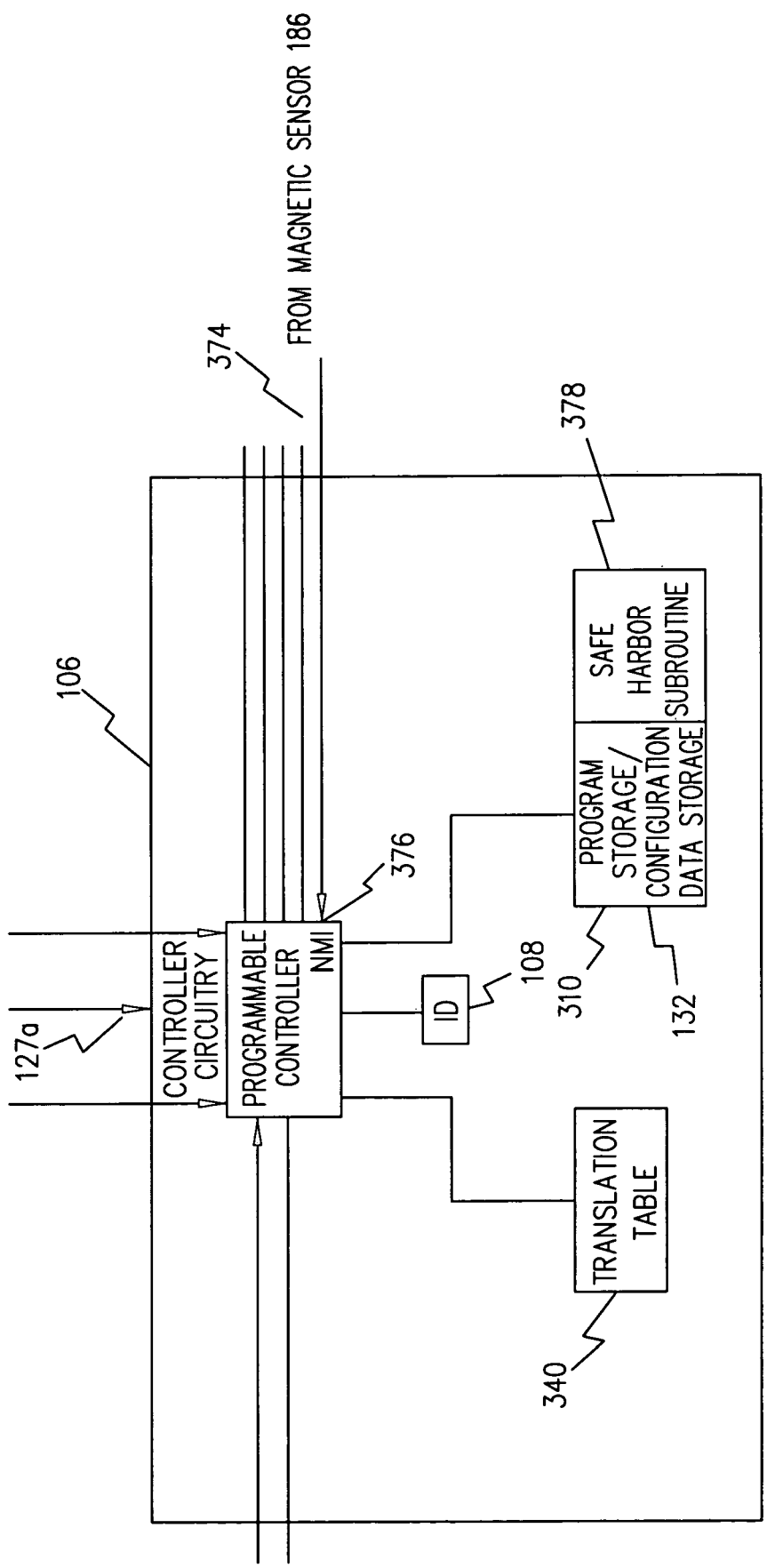

FIG. 3A comprises a block diagram of an exemplary implanted device 100 (as shown in FIG. 2 of the great great grandparent application) which includes a battery 104, preferably rechargeable, for powering the device for a period of time in excess of one hour and responsive to command signals from a remote device, e.g., the SCU 302. As described in the great great grandparent application, the implantable device 100 is preferably configurable to alternatively operate as a microstimulator and/or microsensor and/or microtransponder due to the commonality of most of the circuitry contained within. Such circuitry can be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation, configuration data storage 132 can be alternatively used as the program storage 310 when the implantable device 100 is used as the SCU 302. In this implementation, XMTR 168 corresponds to the signal transmitter 304 and a RCVR 114b corresponds to the signal receiver 306 (preferably operable using sound means via transducer 138) and the RCVR 114a and XMTR 146 correspond to the transceiver 314 (preferably operable using magnetic means via coil 116).

In a preferred embodiment, the contents of the program storage 310, i.e., the software that controls the operation of the programmable controller 308, can be remotely downloaded, e.g., from the clinician's programmer 172 using data modulated onto an AC magnetic field. In this embodiment, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is significant if multiple patient's could be physically located, e.g., in adjoining beds, within the communication range of the clinician's programmer 172.

In a further aspect of the present invention, it is preferable that the SCU 302 be operable for an extended period of time, e.g., in excess of one hour, from an internal power supply 316. While a primary battery, i.e., a nonrechargeable battery, is suitable for this function, it is preferable that the power supply 316 include a rechargeable battery, e.g., battery 104 as described in the great great grandparent application, that can be recharged via an AC magnetic field produced external to the patient's body. Accordingly, the power supply 102 of FIG. 3A (described in detail in the great great grandparent application) is the preferred power supply 316 for the SCU 302 as well.

The battery-powered devices 100 of the great great grandparent invention are preferably configurable to operate in a plurality of operation modes, e.g., via a communicated command signal. In a first operation mode, device 100 is remotely configured to be a microstimulator, e.g., 100a and 100b. In this embodiment, controller 130 commands stimulation circuitry 110 to generate a sequence of drive pulses through electrodes 112 to stimulate tissue, e.g., a nerve, proximate to the implanted location of the microstimulator, e.g., 100a or 100b. In operation, a programmable pulse generator 178 and voltage multiplier 180 are configured with parameters (see Table I) corresponding to a desired pulse sequence and specifying how much to multiply the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby nerve. Alternatively, electrodes can be selected that will form an equivalent capacitor within the body tissue.

TABLE I

Stimulation Parameters

| | |
|---|---|
| Current: | continuous current charging of storage capacitor |
| Charging currents: | 1, 3, 10, 30, 100, 250, 500 µa |
| Current Range: | 0.8 to 40 ma in nominally 3.2% steps |
| Compliance Voltage: | selectable, 3–24 volts in 3 volt steps |
| Pulse Frequency(PPS): | 1 to 5000 PPS in nominally 30% steps |
| Pulse Width: | 5 to 2000 µs in nominally 10% steps |
| Burst On Time (BON): | 1 ms to 24 hours in nominally 20% steps |
| Burst Off Time (BOF): | 1 ms to 24 hours in nominally 20% steps |
| Triggered Delay to BON: | either selected BOF or pulse width |

TABLE I-continued

Stimulation Parameters

| | |
|---|---|
| Burst Repeat Interval: | 1 ms to 24 hours in nominally 20% steps |
| Ramp On Time: | 0.1 to 100 seconds (1, 2, 5, 10 steps) |
| Ramp Off Time: | 0.1 to 100 seconds (1, 2, 5, 10 steps) |

In a next operation mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID stored in address storage circuitry 108, and responsively sends command signals to microstimulators, e.g., 100a and 100b, adjusted accordingly to the sensed data. For example, sensor circuitry 188 can be coupled to the electrodes 112 to sense or otherwise used to measure a biological parameter, e.g., temperature, glucose level, or $O_2$ content and provided the sensed data to controller circuitry 106. Preferably, the sensor circuitry includes a programmable bandpass filter and an analog to digital (A/D) converter that can sense and accordingly convert the voltage levels across the electrodes 112 into a digital quantity. Alternatively, the sensor circuitry can include one or more sense amplifiers to determine if the measured voltage exceeds a threshold voltage value or is within a specified voltage range. Furthermore, the sensor circuitry 188 can be configurable to include integration circuitry to further process the sensed voltage. The operation modes of the sensor circuitry 188 is remotely programmable via the devices communication interface as shown below in Table II.

TABLE II

Sensing Parameters

| | |
|---|---|
| Input voltage range: | 5 μv to 1 V |
| Bandpass filter rolloff: | 24 dB |
| Low frequency cutoff choices: | 3, 10, 30, 100, 300, 1000 Hz |
| High frequency cutoff choices: | 3, 10, 30, 100, 300, 1000 Hz |
| Integrator frequency choices: | 1 PPS to 100 PPS |
| Amplitude threshold for detection choices: | 4 bits of resolution |

Additionally, the sensing capabilities of a microsensor include the capability to monitor the battery status via path 124 from the charging circuit 122 and can additionally include using the ultrasonic transducer 138 or the coil 116 to respectively measure the magnetic or ultrasonic signal magnitudes (or transit durations) of signals transmitted between a pair of implanted devices and thus determine the relative locations of these devices. This information can be used to determine the amount of body movement, e.g., the amount that an elbow or finger is bent, and thus form a portion of a closed loop motion control system.

In another operation mode, the battery-powered implantable device 100 can be configured to operate as a microtransponder, e.g., 100d. In this operation mode, the microtransponder receives (via the aforementioned receiver means, e.g., AC magnetic, sonic, RF or electric) a first command signal from the SCU 302 and retransmits this signal (preferably after reformatting) to other implanted devices (e.g., microstimulators, microsensors, and/or microtransponders) using the aforementioned transmitter means (e.g., magnetic, sonic, RF or electric). While a microtransponder may receive one mode of command signal, e.g., magnetic, it may retransmit the signal in another mode, e.g., ultrasonic. For example, clinician's programmer 172 may emit a modulated magnetic signal using a magnetic emitter 190 to program/command the implanted devices 100. However, the magnitude of the emitted signal may not be sufficient to be successfully received by all of the implanted devices 100. As such, a microtransponder 100d may receive the modulated magnetic signal and retransmit it (preferably after reformatting) as a modulated ultrasonic signal which can pass through the body with fewer restrictions. In another exemplary use, the patient control unit 174 may need to monitor a microsensor 100c in a patient's foot. Despite the efficiency of ultrasonic communication in a patient's body, an ultrasonic signal could still be insufficient to pass from a patient's foot to a patient's wrist (the typical location of the patient control unit 174). As such, a microtransponder 100d could be implanted in the patient's torso to improve the communication link.

Figure 4:
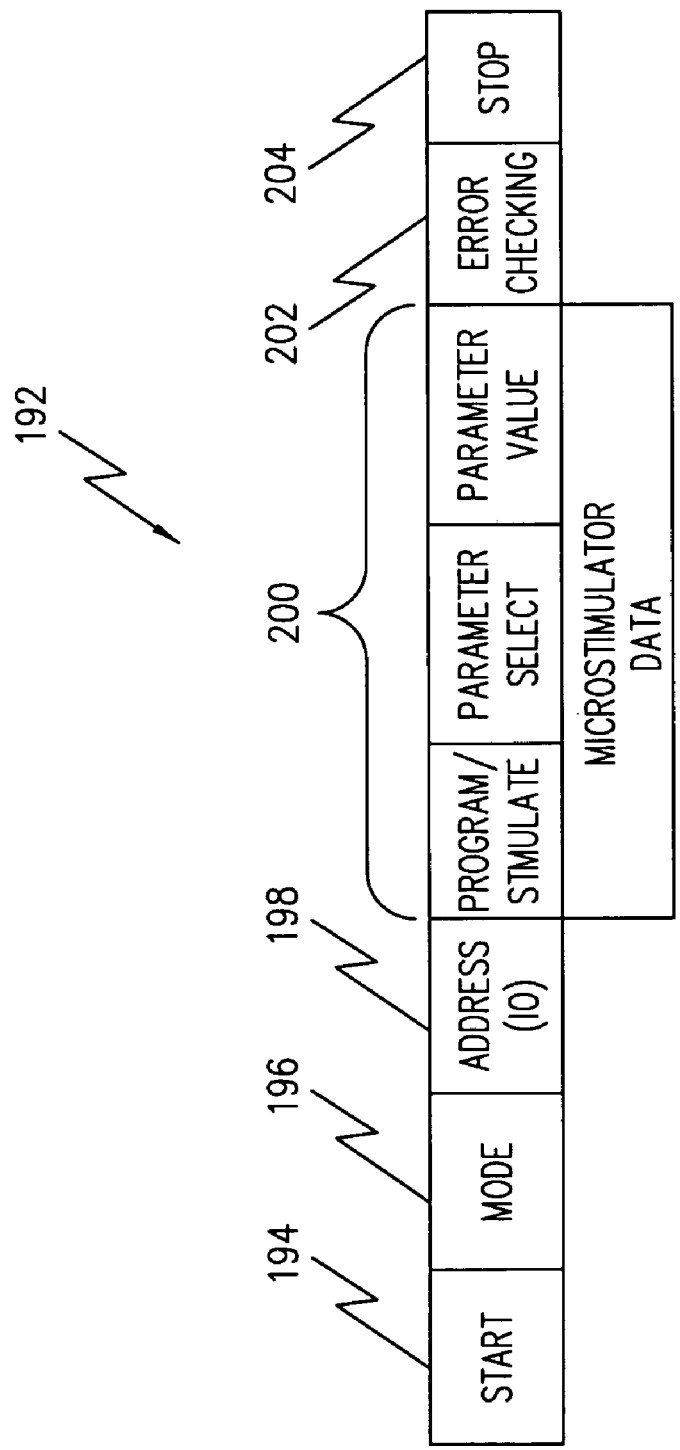
FIG. 4 is a simplified diagram showing the basic format of data messages for commanding/interrogating the implanted microstimulators, microsensors and microtransponders which form a portion of the present invention.

FIG. 4 shows the basic format of an exemplary message 192 for communicating with the aforementioned battery-powered devices 100, all of which are preconfigured with an address (ID), preferably unique to that device, in their address storage circuitry 108 to operate in one or more of the following modes (1) for nerve stimulation, i.e., as a microstimulator, (2) for biological parameter monitoring, i.e., as a microsensor, and/or (3) for retransmitting received signals after reformatting to other implanted devices, i.e., as a microtransponder. The command message 192 is primarily comprised of a (1) start portion 194 (one or more bits to signify the start of the message and to synchronize the bit timing between transmitters and receivers), (2) a mode portion 196 (designating the operating mode, e.g., microstimulator, microsensor, microtransponder, or group mode), (3) an address (ID) portion 198 (corresponding to either the ID in address storage circuitry 108 or a programmed group ID), (4) a data field portion 200 (containing command data for the prescribed operation), (5) an error checking portion 202 (for ensuring the validity of the message 192, e.g., by use of a parity bit), and (6) a stop portion 204 (for designating the end of the message 192). The basic definition of these fields are shown below in Table III. Using these definitions, each device can be separately configured, controlled and/or sensed as part of a system for controlling one or more neural pathways within a patient's body.

TABLE III

Message Data Fields

| MODE | | | ADDRESS (ID) |
|---|---|---|---|
| 00 | = | Stimulator | 8 bit identification address |
| 01 | = | Sensor | 8 bit identification address |
| 02 | = | Transponder | 4 bit identification address |
| 03 | = | Group | 4 bit group identification address |

DATA FIELD PORTION

| | | |
|---|---|---|
| Program/Stimulate | = | select operating mode |
| Parameter/ Preconfiguration Select | = | select programmable parameter in program mode or preconfigured stimulation or sensing parameter in other modes |
| Parameter Value | = | program value |

Additionally, each device 100 can be programmed with a group ID (e.g., a 4 bit value) which is stored in its configuration data storage 132. When a device 100, e.g., a microstimulator, receives a group ID message that matches its stored group ID, it responds as if the message was directed to its ID within its address storage circuitry 108. Accordingly, a plurality of microstimulators, e.g., 100a and 100b, can be commanded with a single message. This mode is of particular use when precise timing is desired among the stimulation of a group of nerves.

The following describes exemplary commands, corresponding to the command message 192 of FIG. 4, which demonstrate some of the remote control/sensing capabilities of the system of devices which comprise the present invention:

Write Command—Set a microstimulator/microsensor specified in the address field 198 to the designated parameter value.

Group Write Command—Set the microstimulators/microsensors within the group specified in the address field 198 to the designated parameter value.

Stimulate Command—Enable a sequence of drive pulses from the microstimulator specified in the address field 198 according to previously programmed and/or default values.

Group Stimulate Command—Enable a sequence of drive pulses from the microstimulators within the group specified in the address field 198 according to previously programmed and/or default values.

Unit Off Command—Disable the output of the microstimulator specified in the address field 198.

Group Stimulate Command—Disable the output of the microstimulators within the group specified in the address field 198.

Read Command—Cause the microsensor designated in the address field 198 to read the previously programmed and/or default sensor value according to previously programmed and/or default values.

Read Battery Status Command—Cause the microsensor designated in the address field 198 to return its battery status.

Define Group Command—Cause the microstimulator/microsensor designated in the address field 198 to be assigned to the group defined in the microstimulator data field 200.

Set Telemetry Mode Command—Configure the microtransponder designated in the address field 198 as to its input mode (e.g., AC magnetic, sonic, etc.), output mode (e.g., AC magnetic, sonic, etc.), message length, etc.

Status Reply Command—Return the requested status/sensor data to the requesting unit, e.g., the SCU.

Download Program Command—Download program/safe harbor routines to the device, e.g., SCU, microstimulator, etc., specified in the address field 198.

Figure 5:
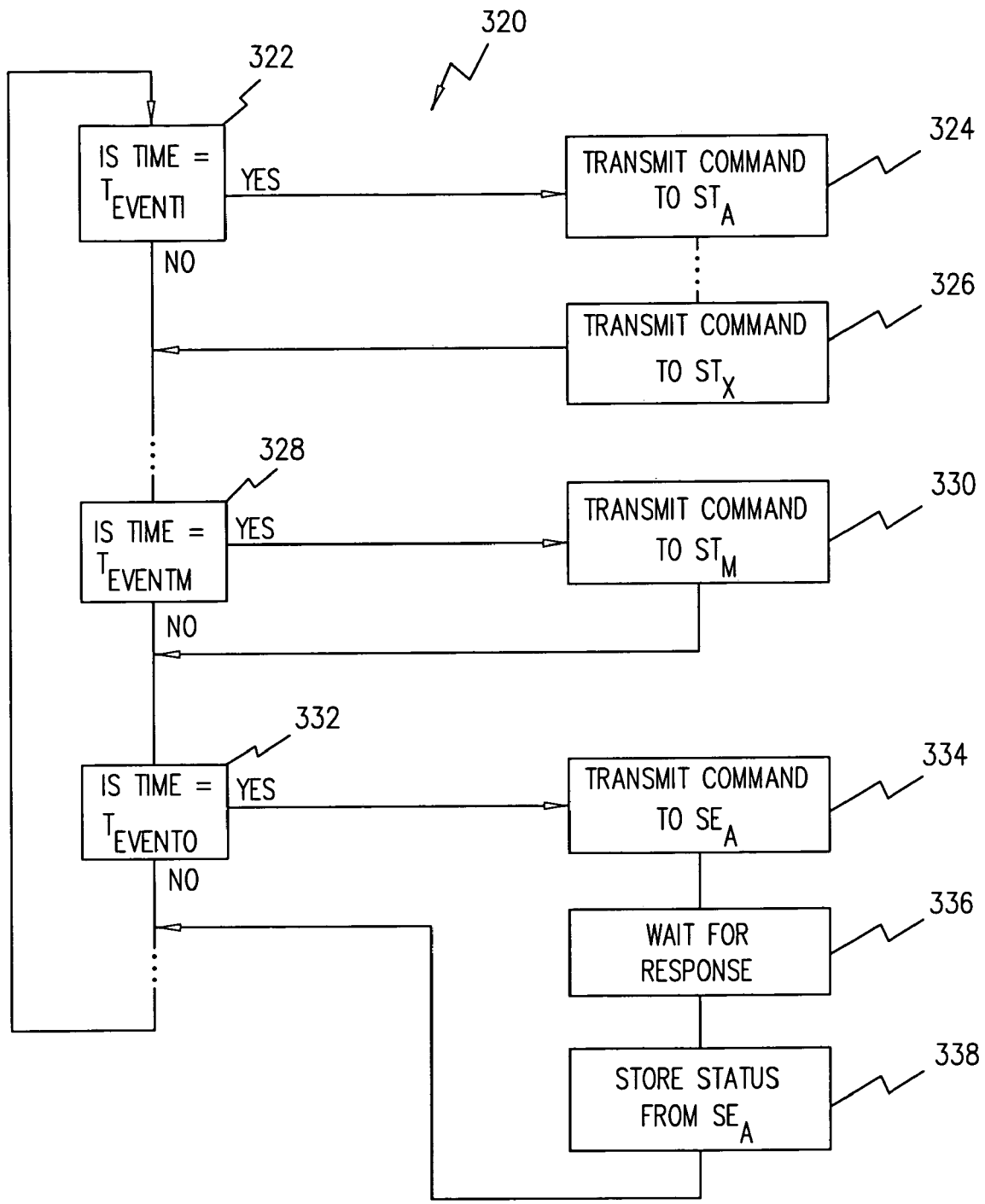
FIG. 5 shows an exemplary flow chart of the use of the present system in an open loop mode for controlling/monitoring a plurality of implanted devices, e.g., microstimulators, microsensors.

FIG. 5 shows a block diagram of an exemplary open loop control program, i.e., a task scheduler 320, for controlling/monitoring a body function/parameter. In this process, the programmable controller 308 is responsive to the clock 312 (preferably crystal controlled to thus permit real time scheduling) in determining when to perform any of a plurality of tasks. In this exemplary flow chart, the programmable controller 308 first determines in block 322 if it is now at a time designated as $T_{EVENT1}$ (or at least within a sampling error of that time), e.g., at 1:00 AM. If so, the programmable controller 308 transmits a designated command to microstimulator A ($ST_A$) in block 324. In this example, the control program continues where commands are sent to a plurality of stimulators and concludes in block 326 where a designated command is sent to microstimulator X ($ST_X$). Such a subprocess, e.g., a subroutine, is typically used when multiple portions of body tissue require stimulation, e.g., stimulating a plurality of muscle groups in a paralyzed limb to avoid atrophy. The task scheduler 320 continues through multiple time event detection blocks until in block 328 it determines whether the time $T_{EVENTM}$ has arrived. If so, the process continues at block 330 where, in this case, a single command is sent to microstimulator M ($ST_M$). Similarly, in block 332 the task scheduler 320 determines when it is the scheduled time, i.e., $T_{EVENTO}$, to execute a status request from microsensor A ($SE_A$). If so, a subprocess, e.g., a subroutine, commences at block 334 where a command is sent to microsensor A ($SE_A$) to request sensor data and/or specify sensing criteria. Microsensor A ($SE_A$) does not instantaneously respond. Accordingly, the programmable controller 308 waits for a response in block 336. In block 338, the returned sensor status data from microsensor A ($SE_A$) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process can be used where the SCU 302 periodically interrogates each implantable device 100 to determine its battery status.

Figure 6:
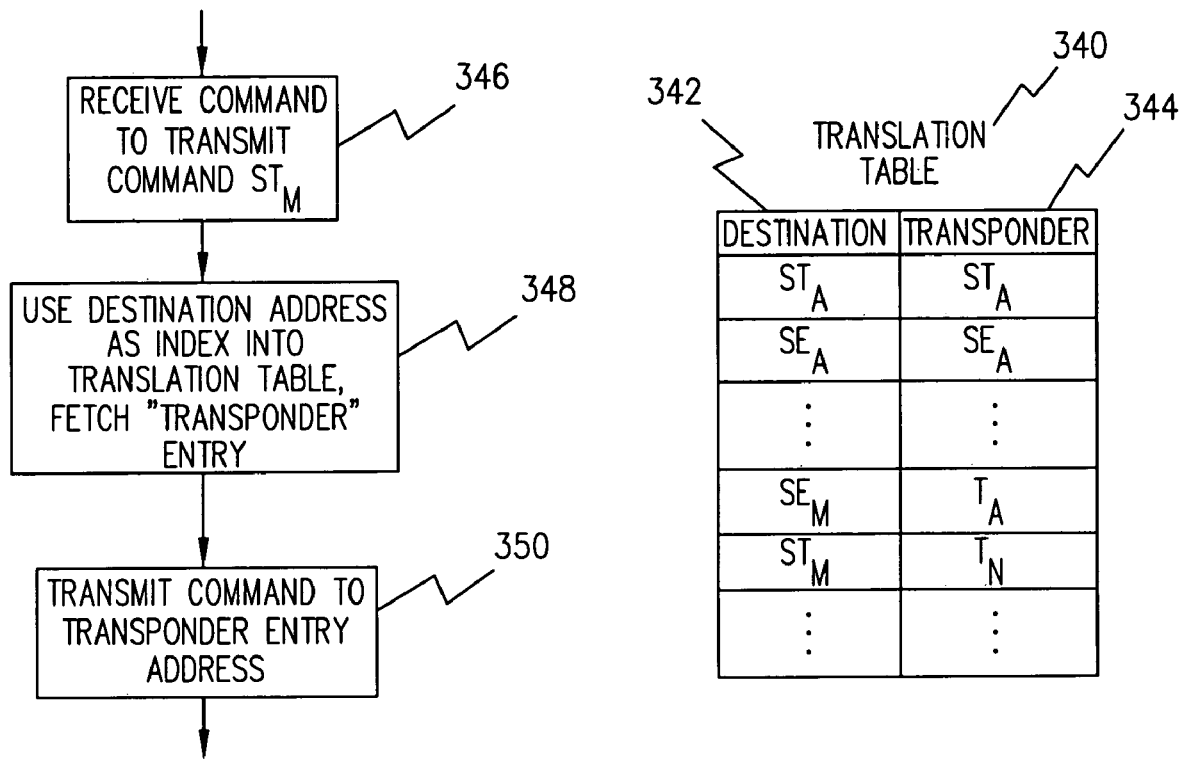
FIG. 6 shows a flow chart of the optional use of a translation table for communicating with microstimulators and/or microsensors via microtransponders.

FIG. 6 shows an exemplary use of an optional translation table 340 for communicating between the SCU 302 and microstimulators, e.g., 100a, and/or microsensors, e.g., 100c, via microtransponders, e.g., 100d. A microtransponder, e.g., 100d, is used when the communication range of the SCU 302 is insufficient to reliably communicate with other implanted devices 100. In this case, the SCU 302 instead directs a data message, i.e., a data packet, to an intermediary microtransponder, e.g., 100d, which retransmits the data packet to a destination device 100. In an exemplary implementation, the translation table 340 contains pairs of corresponding entries, i.e., first entries 342 corresponding to destination addresses and second entries 344 corresponding to the intermediary microtransponder addresses. When the SCU 302 determines, e.g., according to a timed event designated in the program storage 310, that a command is to be sent to a designated destination device (see block 346), the SCU 302 searches the first entries 342 of the translation table 340, for the destination device address, e.g., $ST_M$. The SCU 302 then fetches the corresponding second table entry 344 in block 348 and transmits the command to that address in block 350. When the second table entry 344 is identical to its corresponding first table entry 342, the SCU 302 transmits commands directly to the implanted device 100. However, when the second table entry 344, e.g., $T_N$, is different from the first table entry 342, e.g., $ST_M$, the SCU 302 transmits commands via an intermediary microtransponder, e.g., 100d. The use of the translation table 340 is optional since the intermediary addresses can, instead, be programmed directly into a control program contained in the program storage 310. However, it is preferable to use such a translation table 340 in that communications can be redirected on the fly by just reprogramming the translation table 340 to take advantage of implanted transponders as required, e.g., if communications should degrade and become unreliable. The translation table 340 is preferably contained in programmable memory, e.g., RAM or EPROM, and can be a portion of the program storage 310. While the translation table 340 can be remotely programmed, e.g., via a modulated signal from the clinician's programmer 172, it is also envisioned that the SCU 302 can reprogram the translation table 340 if the communications degrade.

Figure 7:
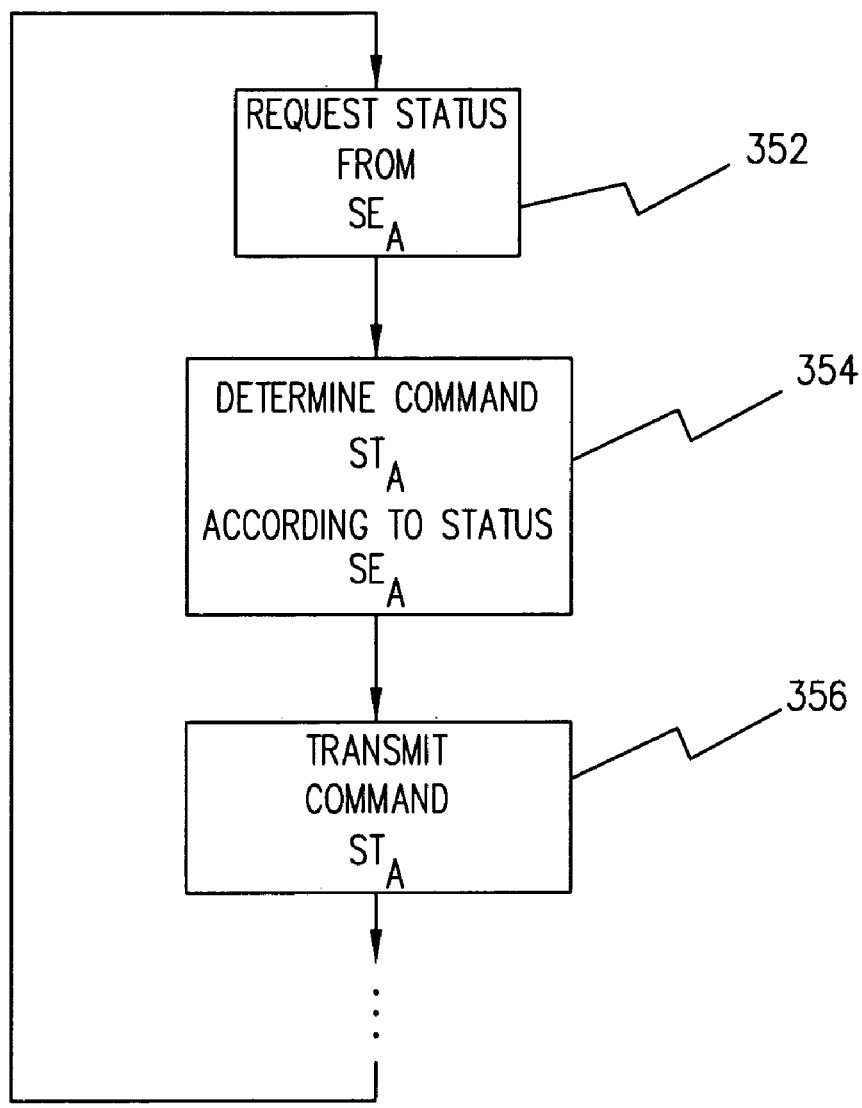
FIG. 7 shows a simplified flow chart of the use of closed loop control of a microstimulator by altering commands from the system control unit in response to status data received from a microsensor.

FIG. 7 is an exemplary block diagram showing the use of the system of the present invention to perform closed loop control of a body function. In block 352, the SCU 302 requests status from microsensor A ($SE_A$). The SCU 302, in block 354, then determines whether a current command given to a microstimulator is satisfactory and, if necessary, determines a new command and transmits the new command to the microstimulator A in block 356. For example, if microsensor A ($SE_A$) is reading a voltage corresponding to a pressure generated by the stimulation of a muscle, the SCU 302 could transmit a command to microstimulator A ($ST_A$) to adjust the sequence of drive pulses, e.g., in magnitude, duty cycle, etc., and accordingly change the voltage sensed by microsensor A ($SE_A$). Accordingly, closed loop, i.e., feedback, control is accomplished. The characteristics of the feedback (position, integral, derivative (PID)) control are preferably program controlled by the SCU 302 according to the control program contained in program storage 310.

Figure 8:
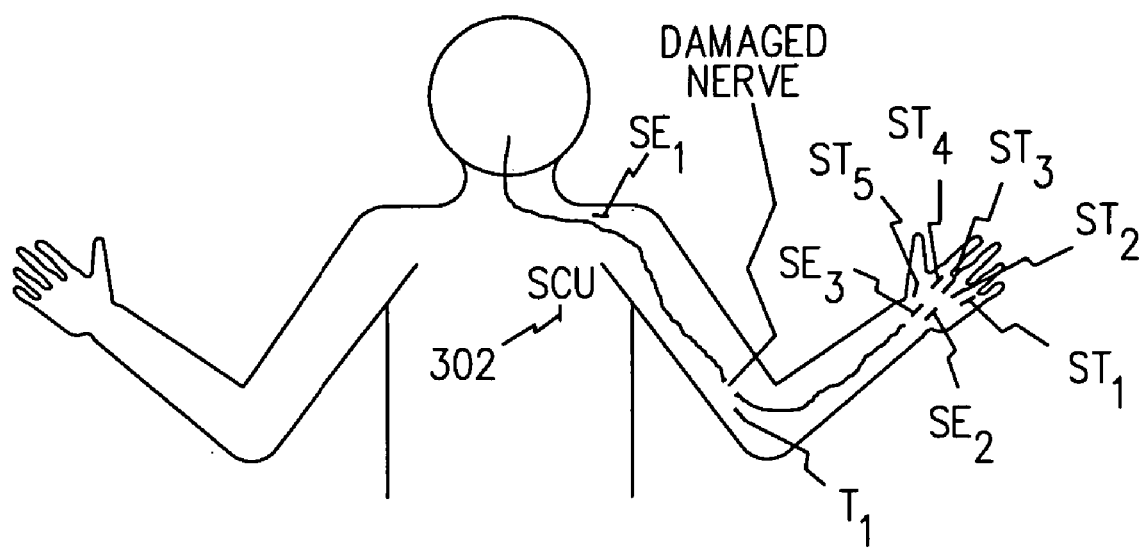
FIG. 8 shows an exemplary injury, i.e., a damaged nerve, and the placement of a plurality of implanted devices, i.e., microstimulators, microsensors and a microtransponder under control of the system control unit for "replacing" the damaged nerve.

FIG. 8 shows an exemplary injury treatable by embodiments of the present system 300. In this exemplary injury, the neural pathway has been damaged, e.g., severed, just above the patient's left elbow. The goal of this exemplary system is to bypass the damaged neural pathway to permit the patient to regain control of the left hand. An SCU 302 is implanted within the patient's torso to control a plurality of stimulators, $ST_1$–$ST_5$, implanted proximate to the muscles respectively controlling the patient's thumb and fingers. Additionally, microsensor 1 ($SE_1$) is implanted proximate to an undamaged nerve portion where it can sense a signal generated from the patient's brain when the patient wants hand closure. Optional microsensor 2 ($SE_2$) is implanted in a portion of the patient's hand where it can sense a signal corresponding to stimulation/motion of the patient's pinky finger and microsensor 3 ($SE_3$) is implanted and configured to measure a signal corresponding to grip pressure generated when the fingers of the patient's hand are closed. Additionally, an optional microtransponder ($T_1$) is shown which can be used to improve the communication between the SCU 302 and the implanted devices.

Figure 9:
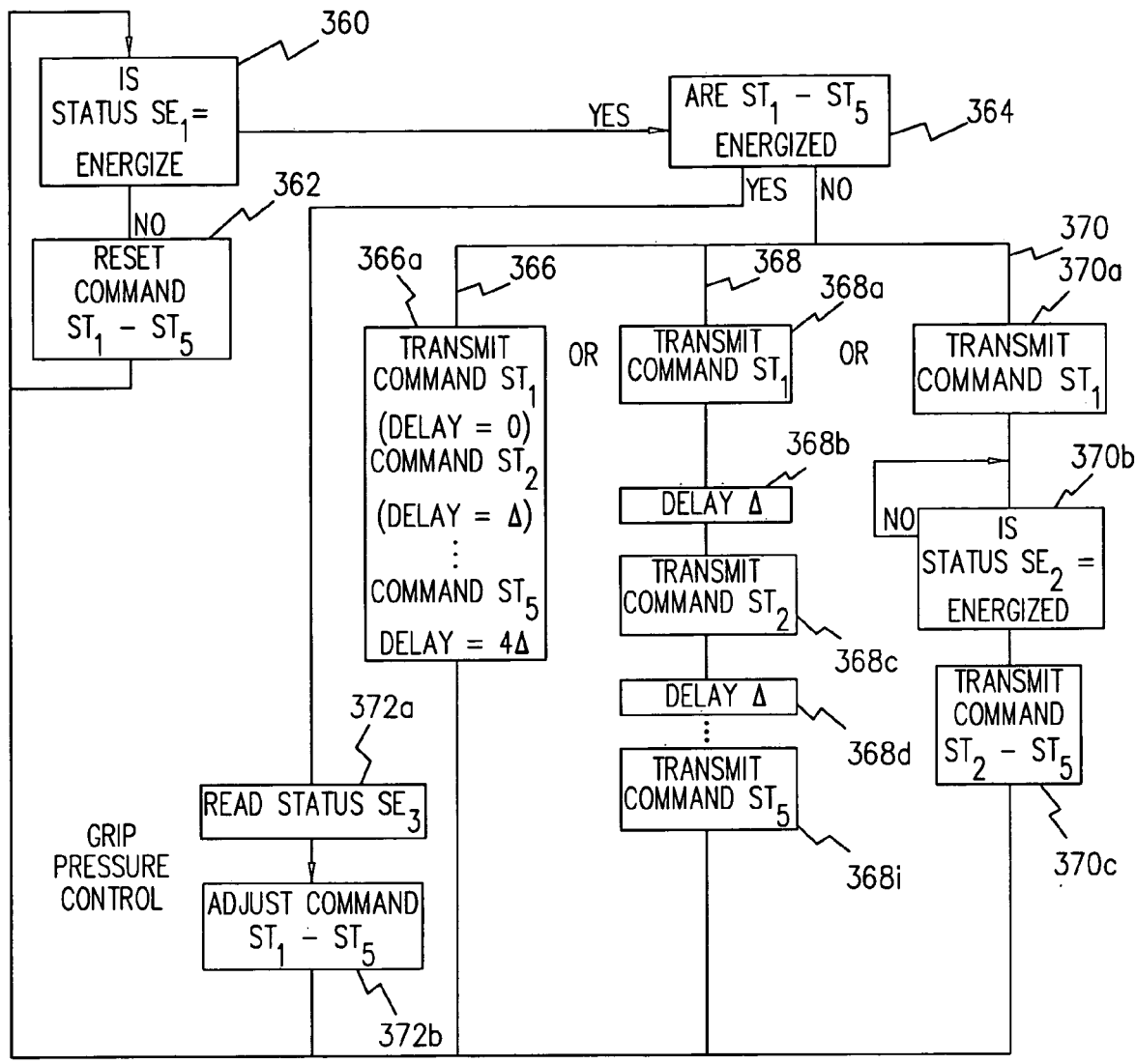
FIG. 9 shows a simplified flow chart of the control of the implanted devices of FIG. 8 by the system control unit.

FIG. 9 shows an exemplary flow chart for the operation of the SCU 302 in association with the implanted devices in the exemplary system of FIG. 8. In block 360, the SCU 302 interrogates microsensor 1 ($SE_1$) to determine if the patient is requesting actuation of his fingers. If not, a command is transmitted in block 362 to all of the stimulators ($ST_1$–$ST_5$) to open the patient's hand, i.e., to de-energize the muscles which close the patient's fingers. If microsensor 1 ($SE_1$) senses a signal to actuate the patient's fingers, the SCU 302 determines in block 364 whether the stimulators $ST_1$–$ST_5$ are currently energized, i.e., generating a sequence of drive pulses. If not, the SCU 302 executes instructions to energize the stimulators. In a first optional path 366, each of the stimulators are simultaneously (subject to formatting and transmission delays) commanded to energize in block 366*a*. However, the command signal given to each one specifies a different start delay time (using the BON parameter). Accordingly, there is a stagger between the actuation/closing of each finger.

In a second optional path 368, the microstimulators are consecutively energized by a delay Δ. Thus, microstimulator 1 ($ST_1$) is energized in block 368*a*, a delay is executed within the SCU 302 in block 368*b*, and so on for all of the microstimulators. Accordingly, paths 366 and 368 perform essentially the same function. However, in path 366 the interdevice timing is performed by the clocks within each implanted device 100 while in path 368, the SCU 302 is responsible for providing the interdevice timing.

In path 370, the SCU 302 actuates a first microstimulator ($ST_1$) in block 370*a* and waits in block 370*b* for its corresponding muscle to be actuated, as determined by microsensor 2 ($SE_2$), before actuating the remaining stimulators ($ST_2$–$ST_5$) in block 370*c*. This implementation could provide more coordinated movement in some situations.

Once the stimulators have been energized, as determined in block 364, closed loop grip pressure control is performed in blocks 372*a* and 372*b* by periodically reading the status of microsensor 3 ($SE_3$) and adjusting the commands given to the stimulators ($ST_1$–$ST_5$) accordingly. Consequently, this exemplary system has enabled the patient to regain control of his hand including coordinated motion and grip pressure control of the patient's fingers.

Referring again to FIG. 3A, a magnetic sensor 186 is shown. In the great great grandparent application, it was shown that such a sensor 186 could be used to disable the operation of an implanted device 100, e.g., to stop the operation of such devices in an emergency situation, in response to a DC magnetic field, preferably from an externally positioned safety magnet 187. A further implementation is disclosed herein. The magnetic sensor 186 can be implemented using various devices. Exemplary of such devices are devices manufactured by Nonvolatile Electronics, Inc. (e.g., their AA, AB, AC, AD, or AG series), Hall effect sensors, and subminiature reed switches. Such miniature devices are configurable to be placed within the housing of the disclosed SCU 302 and implantable devices 100. While essentially passive magnetic sensors, e.g., reed switches, are possible, the remaining devices include active circuitry that consumes power during detection of the DC magnetic field. Accordingly, it is preferred that controller circuitry 302 periodically, e.g., once a second, provide power to the magnetic sensor 186 and sample the sensor's output signal 374 during that sampling period.

In a preferred implementation of the SCU 302, the programmable controller 308 is a microcontroller operating under software control wherein the software is located within the program storage 310. The SCU 302 preferably includes an input 376, e.g., a non maskable interrupt (NMI), which causes a safe harbor subroutine 378, preferably located within the program storage 310, to be executed. Additionally, failure or potential failure modes, e.g., low voltage or over temperature conditions, can be used to cause the safe harbor subroutine 378 to be executed. Typically, such a subroutine could cause a sequence of commands to be transmitted to set each microstimulator into a safe condition for the particular patient configuration, typically disabling each microstimulator. Alternatively, the safe harbor condition could be to set certain stimulators to generate a prescribed sequence of drive pulses. Preferably, the safe harbor subroutine 378 can be downloaded from an external device, e.g., the clinician's programmer 172, into the program storage 310, a nonvolatile storage device. Additionally, it is preferable that, should the programmable contents of the program storage be lost, e.g., from a power failure, a default safe harbor subroutine be used instead. This default subroutine is preferably stored in nonvolatile storage that is not user programmable, e.g., ROM, that is otherwise a portion of the program storage 310. This default subroutine is preferably general purpose and typically is limited to commands that turn off all potential stimulators.

Alternatively, such programmable safe harbor subroutines 378 can exist in the implanted stimulators 100. Accordingly, a safe harbor subroutine could be individually programmed into each microstimulator that is customized for the environment of that individual microstimulator and a safe harbor subroutine for the SCU 302 could then be designated that disables the SCU 302, i.e., causes the SCU 302 to not issue subsequent commands to other implanted devices 100.

FIG. 10A shows a side view of a microstimulator 100 made in accordance with the present invention which includes battery 104 for powering the circuitry within. The battery 104 conveniently fits within a sealed elongate housing 206 (preferably hermetically sealed) which encases the microstimulator 100. In a preferred device 100, the axial dimension 208 is less than 60 mm and the lateral dimension 207 is less than 6 mm.

For the embodiment shown in FIG. 10A, the battery 104 is preferably housed within its own battery case 209, with the battery terminals comprising an integral part of its case 209 (much like a conventional AA battery). Thus, the sides and left end of the battery 104 (as oriented in FIG. 10A) may comprise one battery terminal 210, e.g., the negative battery terminal, and the right end of the battery 104 may comprise the other battery terminal, e.g., the positive battery terminal used as the output terminal 128. Advantageously, because such a battery case 209 is conductive, it may serve as an electrical conductor for connecting an appropriate circuit node for the circuitry within the microstimulator 100 from one side of the battery to the other. More particularly, for the configuration shown in FIG. 1A, the battery terminal 210 may serve as a ground point or node for all of the circuitry housed within the device housing 206. Hence, stem 212 from the electrode 112a on the left end of the microstimulator 100, which from an electrical circuit point of view is simply connected to circuit ground, may simply contact the left end of the battery 104. Then, this same circuit ground connection is made available near or on the rim of the battery 104 on its right side, near one or more IC chips 216 (preferably implementing the device's power consuming circuitry, e.g., the controller 106 and stimulation circuitry 110) on the right side of battery 104 within the right end of the housing 206. By using the conductive case 209 of the battery 104 in this manner, there is no need to try to pass or fit a separate wire or other conductor around the battery 104 to electrically connect the circuitry on the right of the device 100 with the electrode 112a on the left side of the device 100.

FIG. 10B shows a battery powered microstimulator 100' that is substantially the same as the device 100 shown in FIG. 10A except that the microstimulator 100' includes internal coupling capacitor 183 (used to prevent DC current flow through the body tissue). The internal coupling capacitor 183 is used for the embodiment shown in FIG. 10B because both of the microstimulator electrodes 112a and 112b used by the microstimulator 100' are made from the same material, iridium. In contrast, the electrodes 112a and 112b for the microstimulator 100 shown in FIG. 10A are made from different materials, and in particular from iridium (electrode 112b) and tantalum (electrode 112a), and such materials inherently provide a substantial capacitance between them, thereby preventing DC current flow. See, e.g., col. 11, lines 26–33, of U.S. Pat. No. 5,324,316.

Figure 10C:
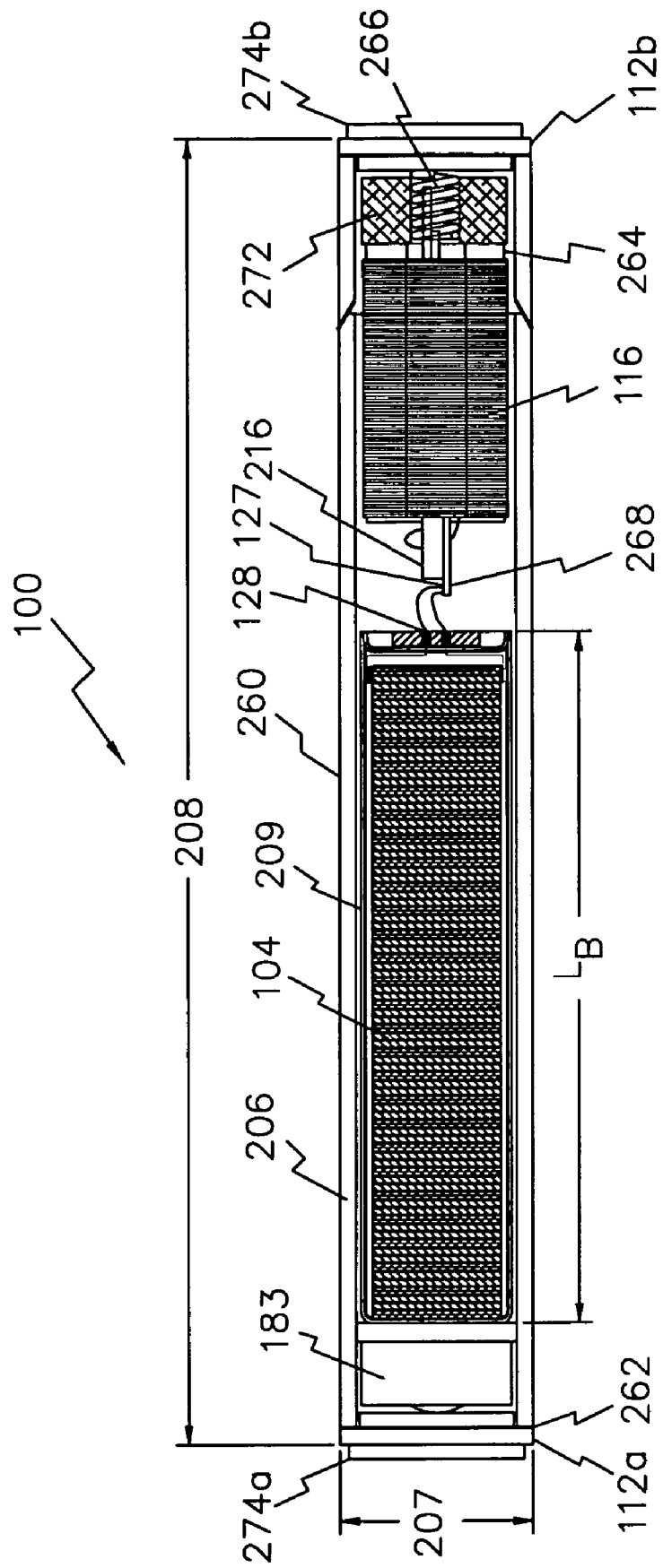
FIGS. 10C and 10D show two side cutaway views of the presently preferred embodiment of an implantable ceramic tube suitable for housing the system control unit and/or microstimulators and/or microsensors and/or microtransponders.
Figure 10D:
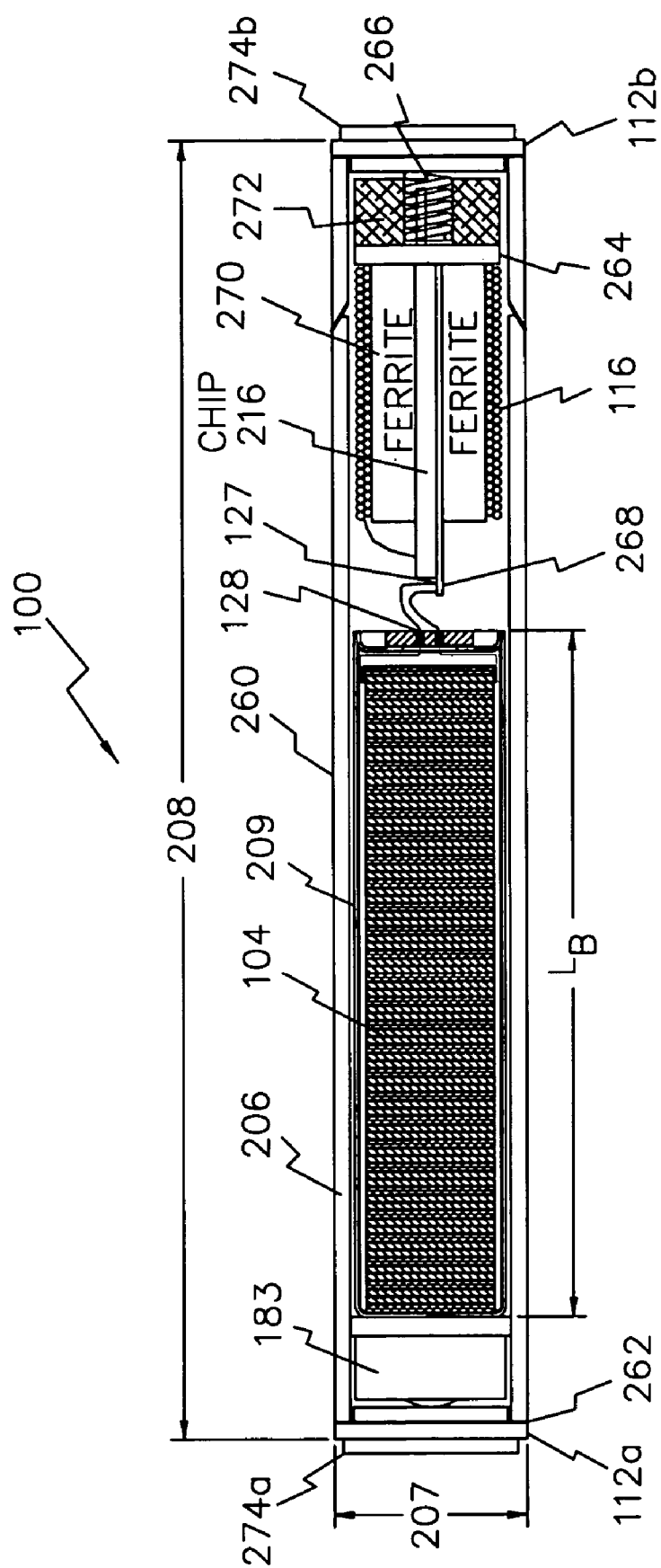

FIGS. 10C and 10D show two side cutaway views of the presently preferred construction of the sealed housing 206, the battery 104 and the circuitry (implemented on one or more IC chips 216 to implement electronic portions of the SCU 302) contained within. In this presently preferred construction, the housing 206 is comprised of an insulating ceramic tube 260 brazed onto a first end cap forming electrode 112a via a braze 262. At the other end of the ceramic tube 260 is a metal ring 264 that is also brazed onto the ceramic tube 260. The circuitry within, i.e., a capacitor 183 (used when in a microstimulator mode), battery 104, IC chips 216, and a spring 266 is attached to an opposing second end cap forming electrode 112b. A drop of conductive epoxy is used to glue the capacitor 183 to the end cap 112a and is held in position by spring 266 as the glue takes hold. Preferably, the IC chips 216 are mounted on a circuit board 268 over which half circular longitudinal ferrite plates 270 are attached. The coil 116 is wrapped around the ferrite plates 270 and attached to IC chips 216. A getter 272, mounted surrounding the spring 266, is preferably used to increase the hermeticity of the SCU 302 by absorbing water introduced therein. An exemplary getter 272 absorbs 70 times its volume in water. While holding the circuitry and the end cap 112b together, one can laser weld the end cap 112b to the ring 264. Additionally, a platinum, iridium, or platinum-iridium disk or plate 274 is preferably welded to the end caps of the SCU 302 to minimize the impedance of the connection to the body tissue.

An exemplary battery 104 is described more fully below in connection with the description of FIG. 11. Preferably, the battery 104 is made from appropriate materials so as to provide a power capacity of at least 1 microwatt-hour, preferably constructed from a battery having an energy density of about 240 mW-Hr/cm$^3$. A Li—I battery advantageously provides such an energy density. Alternatively, an Li—I—Sn battery provides an energy density up to 360 mW-Hr/cm$^3$. Any of these batteries, or other batteries providing a power capacity of at least 1 microwatt-hour may be used with implanted devices of the present invention.

The battery voltage V of an exemplary battery is nominally 3.6 volts, which is more than adequate for operating the CMOS circuits preferably used to implement the IC chip(s) 216, and/or other electronic circuitry, within the SCU 302. The battery voltage V, in general, is preferably not allowed to discharge below about 2.55 volts, or permanent damage may result. Similarly, the battery 104 should preferably not be charged to a level above about 4.2 volts, or else permanent damage may result. Hence, a charging circuit 122 (discussed in the great great grandparent application) is used to avoid any potentially damaging discharge or overcharge.

The battery 104 may take many forms, any of which may be used so long as the battery can be made to fit within the small volume available. As previously discussed, the battery 104 may be either a primary battery or a rechargeable battery. A primary battery offers the advantage of a longer life for a given energy output but presents the disadvantage of not being rechargeable (which means once its energy has been used up, the implanted device no longer functions). However, for many applications, such as one-time-only muscle rehabilitation regimens applied to damaged or weakened muscle tissue, the SCU 302 and/or devices 100 need only be used for a short time (after which they can be explanted and discarded, or simply left implanted as benign medical devices). For other applications, a rechargeable battery is clearly the preferred type of energy choice, as the tissue stimulation provided by the microstimulator is of a recurring nature.

The considerations relating to using a rechargeable battery as the battery 104 of the implantable device 100 are presented, inter alia, in the book, *Rechargeable Batteries, Applications Handbook*, EDN Series for Design Engineers, Technical Marketing Staff of Gates Energy Products, Inc. (Butterworth-Heinemann 1992). The basic considerations for any rechargeable battery relate to high energy density and long cycle life. Lithium based batteries, while historically used primarily as a nonrechargeable battery, have in recent years appeared commercially as rechargeable batteries. Lithium-based batteries typically offer an energy density of from 240 mW-Hr/cm$^3$ to 360 mW-Hr/cm$^3$. In general, the higher the energy density the better, but any battery construction exhibiting an energy density resulting in a power capacity greater than 1 microwatt-hour is suitable for the present invention.

One of the more difficult hurdles facing the use of a battery 104 within the SCU 302 relates to the relatively small size or volume inside the housing 206 within which the battery must be inserted. A typical SCU 302 made in accordance with the present invention is no larger than about 60 mm long and 8 mm in diameter, preferably no larger than 60 mm long and 6 mm in diameter, and includes even smaller embodiments, e.g., 15 mm long with an O.D. of 2.2 mm (resulting in an I.D. of about 2 mm). When one considers that only about ¼ to ½ of the available volume within the device housing 206 is available for the battery, one begins to appreciate more fully how little volume, and thus how little battery storage capacity, is available for the SCU 302.

Figure 11:
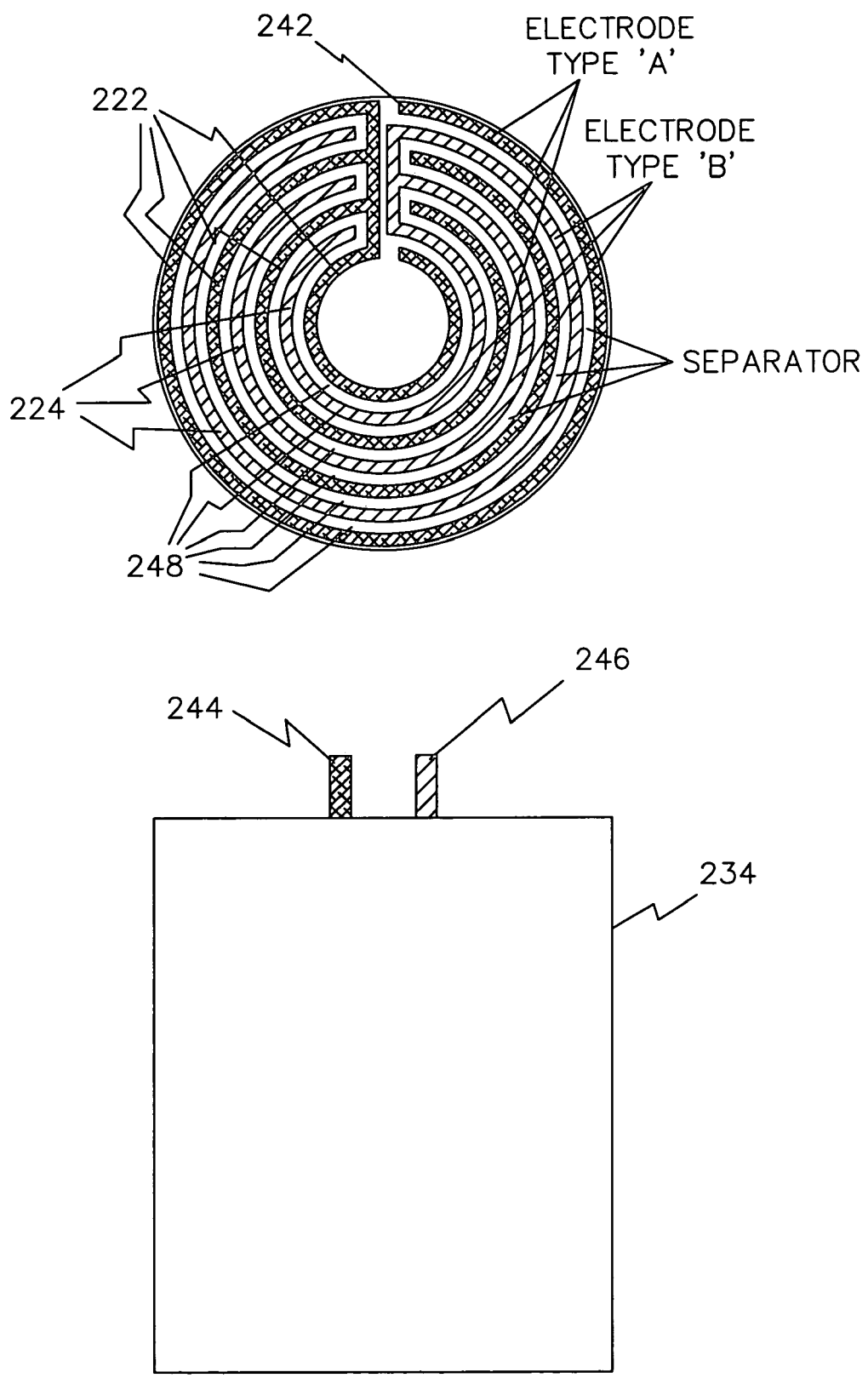
FIG. 11 illustrates an exemplary battery suitable for powering the implantable devices which comprise the components of the present invention.

FIG. 11 shows an exemplary battery 104 typical of those disclosed in the great great grandparent application. Specifically, a parallel-connected cylindrical electrode embodiment is shown where each cylindrical electrode includes a gap or slit 242; with cylindrical electrodes 222 and 224 on each side of the gap 242 forming a common connection point for tabs 244 and 246 which serve as the electrical terminals for the battery. The electrodes 222 and 224 are separated by a suitable separator layer 248. The gap 242 minimizes the flow of eddy currents in the electrodes. For this embodiment, there are four concentric cylindrical electrodes 222, the outer one (largest diameter) of which may function as the battery case 234, and three concentric electrodes 224 interleaved between the electrodes 222, with six concentric cylindrical separator layers 248 separating each electrode 222 or 224 from the adjacent electrodes.

Accordingly, a preferred embodiment of the present invention is comprised of an implanted SCU 302 and a plurality of implanted devices 100, each of which contains its own rechargeable battery 104. As such, a patient is essentially independent of any external apparatus between battery chargings (which generally occur no more often than once an hour). However, for some treatment regimen, it may be adequate to use a power supply analogous to that described in U.S. Pat. No. 5,324,316 that only provides power while an external AC magnetic field is being provided, e.g., from charger 118. Additionally, it may be desired, e.g., from a cost standpoint, to implement the SCU 302 as an external device, e.g., within a watch-shaped housing that can be attached to a patient's wrist in a similar manner to the patient control unit 174.

Figure 12:
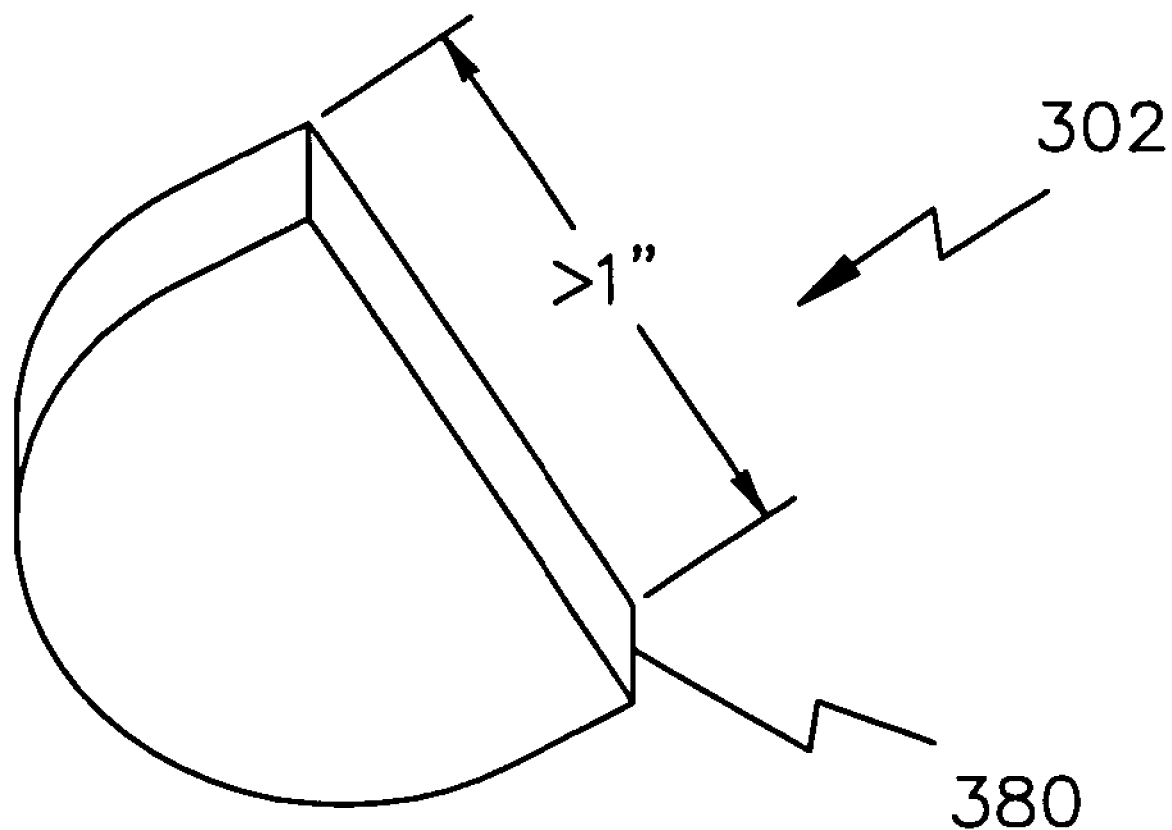
FIG. 12 shows an exemplary housing suitable for an implantable SCU having a battery enclosed within that has a capacity of at least 1 watt-hour.

The power consumption of the SCU 302 is primarily dependent upon the circuitry implementation, preferably CMOS, the circuitry complexity and the clock speed. For a simple system, a CMOS implemented state machine will be sufficient to provide the required capabilities of the programmable controller 308. However, for more complex systems, e.g., a system where an SCU 302 controls a large number of implanted devices 100 in a closed loop manner, a microcontroller may be required. As the complexity of such microcontrollers increases (along with its transistor count), so does its power consumption. Accordingly, a larger battery having a capacity of 1 watt-hour is preferred. While a primary battery is possible, it is preferable that a rechargeable battery be used. Such larger batteries will require a larger volume and accordingly, cannot be placed in the injectable housing described above. However, a surgically implantable device within a larger sealed housing, e.g., having at least one dimension in excess of 1 inch, will serve this purpose when used in place of the previously discussed injectable housing 206. FIG. 12 shows an exemplary implantable housing 380 suitable for such a device.

Figure 13:
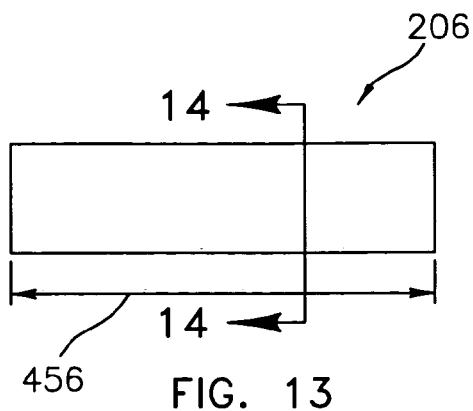
FIG. 13 is an alternative embodiment of the housing of FIGS. 10A–10D.
Figure 14:
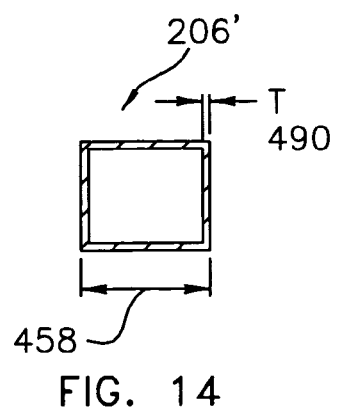
FIG. 14 is a cross-sectional view of the housing of FIG. 13 taken along line 14—14.

While embodiments with a circular cross section are presently preferred, embodiments with a non-circular cross section are also envisioned. As will be discussed further below, non-circular cross sections are selected from the group consisting of rectangular, triangular, oval, hexagonal, octagonal and polygon shaped. Non-circular cross sections allow additional manufacturing alternatives. Additionally, while it is not believed that devices with circular cross sections will migrate significantly after implantation, it is believed that devices with non-circular cross sections will migrate even less and thus may allow a more precise and stable implantation near nerve or muscle tissue and thus may present additional benefits, e.g., higher sensing sensitivity or lower stimulation power and thus longer battery life between chargings. Alternative non-circular embodiments of the housing 206 of microstimulator 100, contemplated by the present invention, are shown in FIGS. 13–24. More specifically, FIG. 13 shows a schematic representation of housing 206', having a square cross-section (see FIG. 14) without expressly showing the inclusion of the internal elements of the microstimulator 100. It is to be understood that operation of the microstimulator 100, including the electrode structure for contact with body tissue, is configured and functions in accordance with the invention described herein independent of the shape of the housing 206, and thus need not be repeated for each housing shape embodiment. The lengthwise dimension 456 may be greater than 60 mm, e.g., in the range of about 60 mm to 70 mm, and the lateral dimension 458 may be greater than 6 mm, e.g., in the range of about 6 mm to 7 mm. The lengthwise dimension 456 and the lateral dimension 458 are preferably selected from the following dimensional groupings: a) lengthwise dimension 456 being less than 60 mm and lateral dimension 458 being greater than or equal to 6 mm; b) lengthwise dimension 456 being greater than 60 mm and lateral dimension 458 being less than or equal to 6 mm; and c) lengthwise dimension 456 being less than or equal to 60 mm and lateral dimension 458 being less than or equal to 6 mm.

Figure 15:
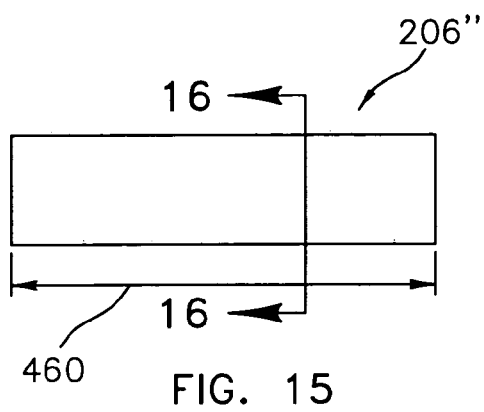
FIG. 15 is an alternative embodiment of the housing of FIGS. 10A–10D.
Figure 16:
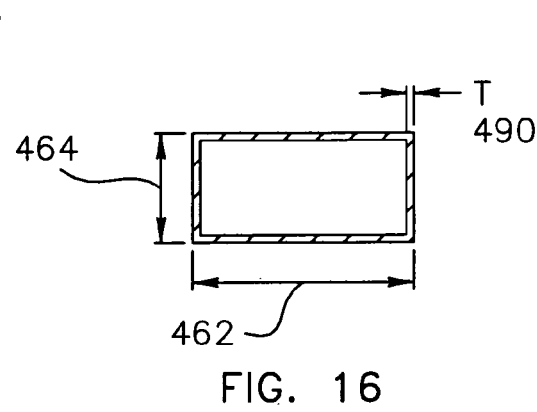
FIG. 16 is a cross-sectional view of the housing of FIG. 15 taken along line 16—16.

With reference to FIG. 15 and the cross-sectional view of FIG. 16, there is shown yet another housing embodiment 206". The housing 206" is rectangular in cross-section having a lengthwise dimension 260 which may be greater than 60 mm and preferably is in the range of 60 mm to 70 mm. A lateral dimension 462 may be greater than 6 mm and preferably is in the range of 6 mm to 7 mm. The lengthwise dimension 460 and the major lateral dimension 462 are preferably selected from the following dimensional groupings: d) lengthwise dimension 460 being less than 60 mm and major lateral dimension 462 being greater than or equal to 6 mm; e) lengthwise dimension 460 being greater than 60 mm and major lateral dimension 462 being less than or equal to 6 mm; and f) lengthwise dimension 460 being less than or equal to 60 mm and major lateral dimension 462 being less than or equal to 6 mm. Similarly, minor lateral dimension 464 may be less than or greater than 6 mm and preferably is in the range of 6 mm to 7 mm.

Figure 17:
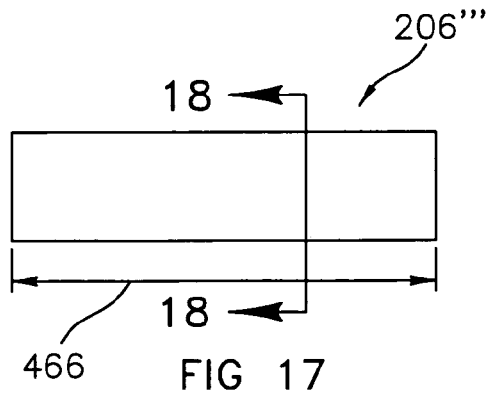
FIG. 17 is an alternative embodiment of the housing of FIGS. 10A–10D.
Figure 18:
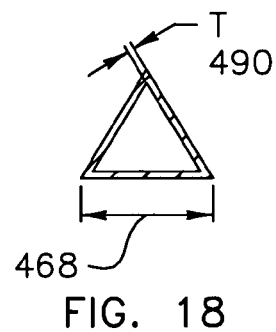
FIG. 18 is a cross-sectional view of the housing of FIG. 17 taken along line 18—18.

With reference to FIG. 17 and the cross-sectional view of FIG. 18, there is shown still yet another housing embodiment 206'''. The housing 206''' is triangular in cross-section having a lengthwise dimension 466 which may be greater than 60 mm and preferably is in the range of 60 mm to 70 mm and a lateral dimension 468 which may be greater than 6 mm and preferably in the range of 6 mm to 7 mm. The lengthwise dimension 466 and the lateral dimension 468 are preferably selected from the following dimensional groupings: g) lengthwise dimension 466 being less than 60 mm and lateral dimension 468 being greater than or equal to 6 mm; h) lengthwise dimension 466 being greater than 60 mm and lateral dimension 468 being less than or equal to 6 mm; and i) lengthwise dimension 466 being less than or equal to 60 mm and lateral dimension 468 being less than or equal to 6 mm.

Figure 19:
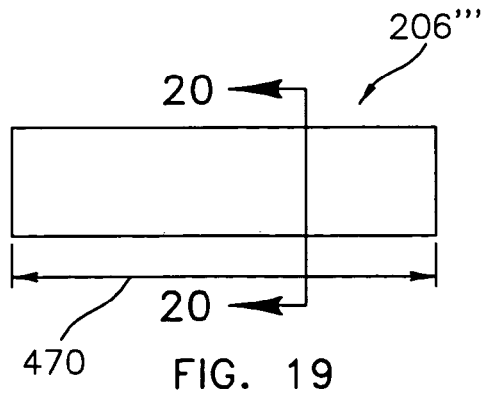
FIG. 19 is an alternative embodiment of the housing of FIGS. 10A–10D.
Figure 20:
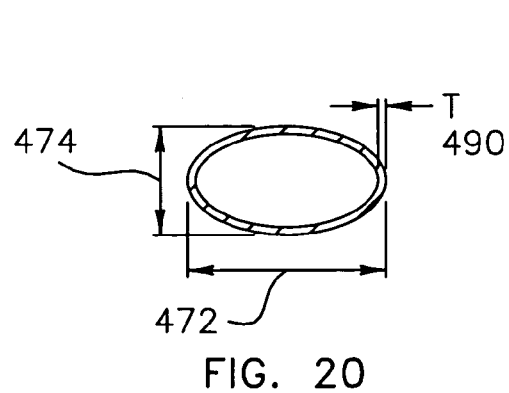
FIG. 20 is a cross-sectional view of the housing of FIG. 19 taken along line 20—20.

With reference to FIG. 19 and the cross-sectional view of FIG. 20, there is shown a still further housing embodiment 206″″. The housing 206″″ is oval in cross-section having a lengthwise dimension 470 which may be greater than 60 mm and preferably is in the range of 60 mm to 70 mm and a major lateral dimension 472 which may be greater than 6 mm and preferably is in the range of about 6 mm to 7 mm and minor lateral dimension 474 of about 6 mm and preferably is in the range of about 6 mm to 7 mm. The lengthwise dimension 470 and the major lateral dimension 472 are preferably selected from the following dimensional groupings: j) lengthwise dimension 470 being less than 60 mm and major lateral dimension 472 being greater than or equal to 6 mm; k) lengthwise dimension 470 being greater than 60 mm and major lateral dimension 472 being less than or equal to 6 mm; and l) lengthwise dimension 470 being less than or equal to 60 mm and major lateral dimension 472 being less than or equal to 6 mm.

Figure 21:
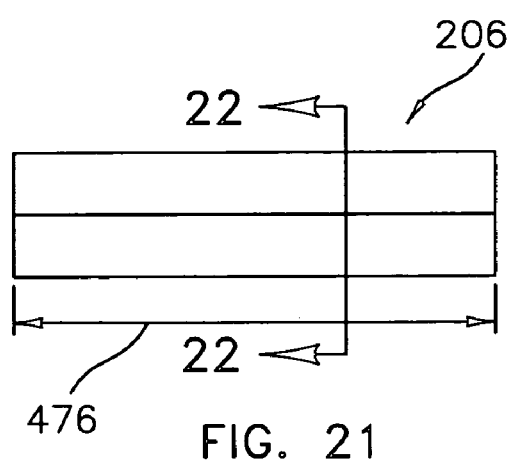
FIG. 21 is an alternative embodiment of the housing of FIGS. 10A–10D.
Figure 22:
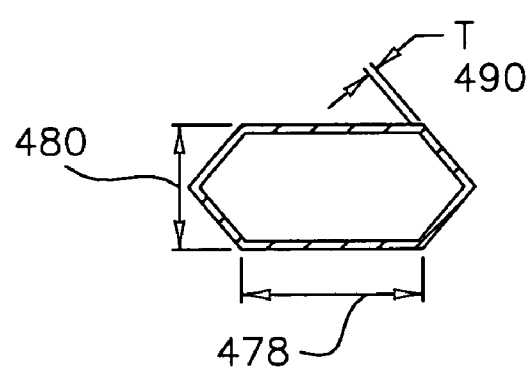
FIG. 22 is a cross-sectional view of the housing of FIG. 21 taken along line 22—22.

With reference to FIG. 21 and the cross-sectional view of FIG. 22, there is shown a further housing embodiment 206″″′. The housing 206″″′ is hexagonal in cross-section having a lengthwise dimension 476 which may be greater than 60 mm and preferably is in the range of 60 mm to 70 mm, a major lateral dimension 478 which may be greater than 6 mm and preferably is in the range of 6 mm to 7 mm and a minor lateral dimension 480 of about 6 mm and preferably is in the range of about 6 mm to 7 mm. The lengthwise dimension 476 and the major lateral dimension 478 are preferably selected from the following dimensional groupings: m) lengthwise dimension 476 being less than 60 mm and major lateral dimension 478 being greater than or equal to 6 mm; n) lengthwise dimension 476 being greater than 60 mm and major lateral dimension 478 being less than or equal to 6 mm; and o) lengthwise dimension 476 being less than or equal to 60 mm and major lateral dimension 478 being less than or equal to 6 mm.

Figure 23:
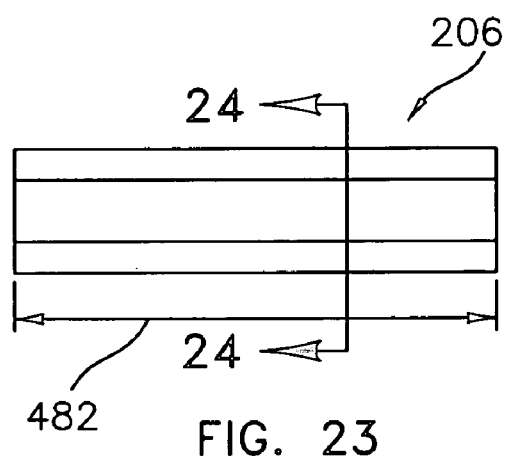
FIG. 23 is an alternative embodiment of the housing of FIGS. 10A–10D.
Figure 24:
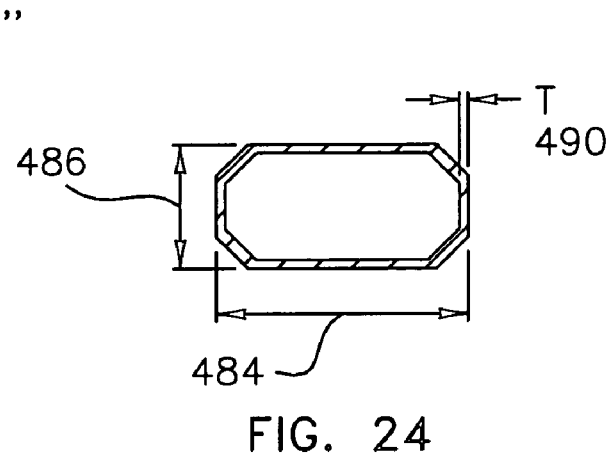
FIG. 24 is a cross-sectional view of the housing of FIG. 23 taken along line 24—24.

With reference to FIG. 23 and the cross-sectional view of FIG. 24, there is shown a still further housing embodiment 206″″″. The housing 206″″″ is octagonal in cross-section having a lengthwise dimension 482 which may be greater than 60 mm and preferably is in the range of 60 mm to 70 mm, a major lateral dimension 484 which may be greater than 6 mm and preferably is in the range of 6 mm to 7 mm, and a minor lateral dimension 486 of about 6 mm and preferably is in the range of about 6 mm to 7 mm. The lengthwise dimension 482 and the major lateral dimension 484 are preferably selected from the following dimensional groupings: p) lengthwise dimension 482 being less than 60 mm and major lateral dimension 484 being greater than or equal to 6 mm; q) lengthwise dimension 482 being greater than 60 mm and major lateral dimension 484 being less than or equal to 6 mm; and r) lengthwise dimension 482 being less than or equal to 60 mm and major lateral dimension 484 being less than or equal to 6 mm.

Preferably, as identified in FIGS. 14, 16, 18, 20, 22, and 24, the housing wall thickness T (290) is in the range of about 1 mm to 4 mm. Moreover, although the cross-sectional views of the housings of FIGS. 14, 16, 18, 20, 22, and 24 appear to have sharp corners, it is to be understood that rounded corners are also contemplated by the invention. As can be appreciated, rounded corners for the housing, facilitate manufacture of the housing as well as the implantation of the microstimulator 100. The dimensional groupings for the housing as presented above provide significant flexibility in configuring the microstimulator 100 to house alternative arrangements of the microstimulator's internal and external electrical and/or mechanical parts.

While various implantable devices have been shown and described having cylindrical and non-cylindrical cross sections, it is to be understood that other polygon shaped cross sections that have not been specifically mentioned are also considered to be within the scope of the present invention. For example, various polygon shaped cross sections have been specifically shown, i.e., triangular (3 sided), rectangular (4 sided), hexagonal (6 sided), and octagonal (8 sided) shapes have been already shown and described but other polygon shaped cross sections are also considered to be within the scope of the present invention, e.g., pentagonal (5 sided), 7 sided, and 9 or more sided polygons. Additionally, while not expressly discussed so far, it is to be recognized by one of ordinary skill in the art that the inner cross sectional shape of the insertion tool 176 is preferably altered to accommodate devices with non-cylindrical cross sections, e.g., a square shape for a square shaped device, triangular shaped for a triangular shaped device, etc.

FIGS. 25–34 are directed to a placement structure 500 that is useful for placing and retaining one of the aforementioned implantable devices 100 in close proximity to a nerve, muscle tissue, or the like, i.e., neural/muscular tissue. For the purposes of this application neural/muscular tissue is understood to signify tissue that passes or responds to neural signals which includes nerve fibers or muscle tissue or any combination thereof. This structure 500 may present additional benefits, e.g., higher sensing sensitivity or lower stimulation power and thus longer battery life between chargings. The placement structure 500 is preferably comprised of two main portions: (1) a holder 502 for holding and retaining the implantable device 100 within and (2) one or more sets (e.g., pairs) of wings 504 for capturing neural/muscular tissue. Preferably, the placement structure 500 is primarily formed from of a biocompatible plastic, e.g., silastic, that is elastic and is also an electrical insulator. In an exemplary embodiment, the holder 502 is essentially semicircular in cross section and has a hollow cavity 506 having end plates 508 and 510 that essentially conforms to the size and shape of implantable device 100 such that the implantable device 100 may be snapped into the cavity 506 and is held by the elasticity of the holder 502 (see FIGS. 25 and 26 which show the insertion of the implantable device 100 into the cavity 506 of the holder 502 of the placement structure 500. It should be noted that while the exemplary capture device 500 is shown for holding an implantable device 100 having a circular cross section, it should be readily apparent to one of ordinary skill in the art that this exemplary structure is readily alterable to accommodate devices having non-circular cross sections as well.

Figure 27:
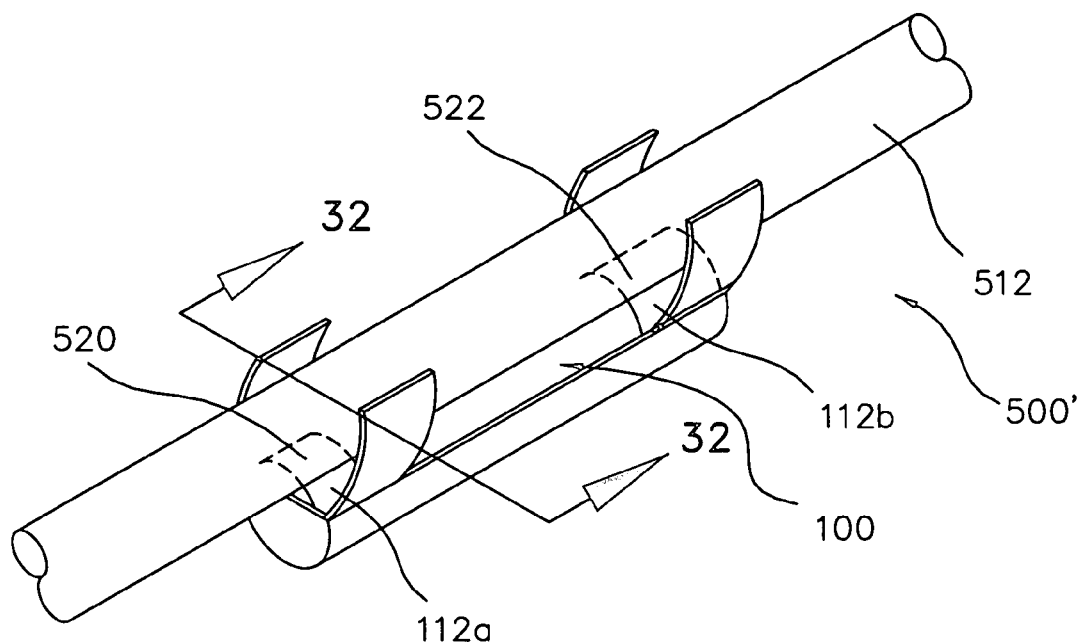
FIG. 27 is a perspective view of the placement structure of FIGS. 25 and 26 showing its wings capturing neural/muscular tissue.
Figure 32:
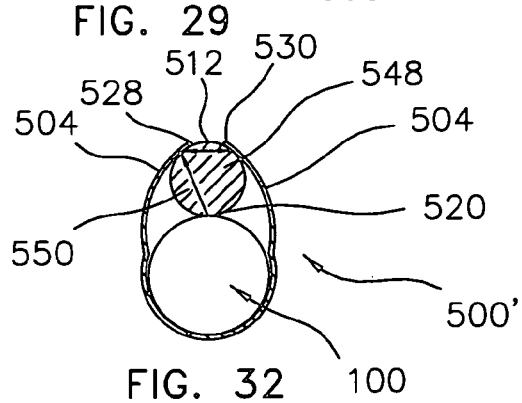
FIG. 32 is a cross sectional view of that shown in FIG. 27 along the line 32—32 showing the wings of the placement structure holding neural/muscular tissue and the resulting stimulation/sensing vectors.

With the implantable device 100 within the cavity 506, the placement structure 500 may be placed in contact, e.g., snapped around, with neural/muscular 512 tissue using the elasticity of the wings 504 to capture/grab the neural/muscular tissue 512 (see FIG. 27, also see the cross sectional view of FIG. 32). As noted in FIGS. 28 and 29, preferred embodiments include structures that rely upon the elasticity of the wings 504 to capture/grab the neural/muscular tissue (see FIG. 28) as well as structures that include hook elements 514 that further supplement the elasticity of the wings 504 for capturing/grabbing the neural/muscular tissue 512.

Figure 30:
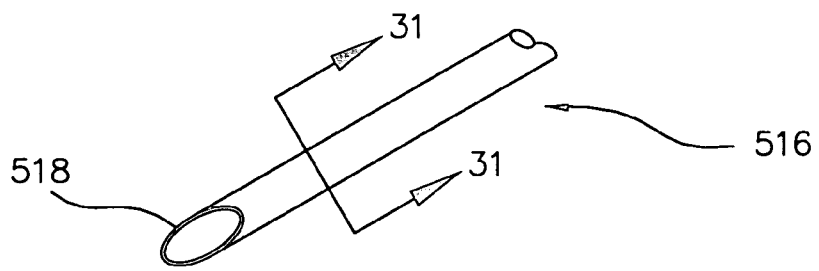
FIG. 30 is an exemplary laparoscopic device suitable for implanting the placement structure of the present invention which in turn is holding one of the aforementioned implantable devices in close proximity to neural/muscular tissue.
Figure 33:
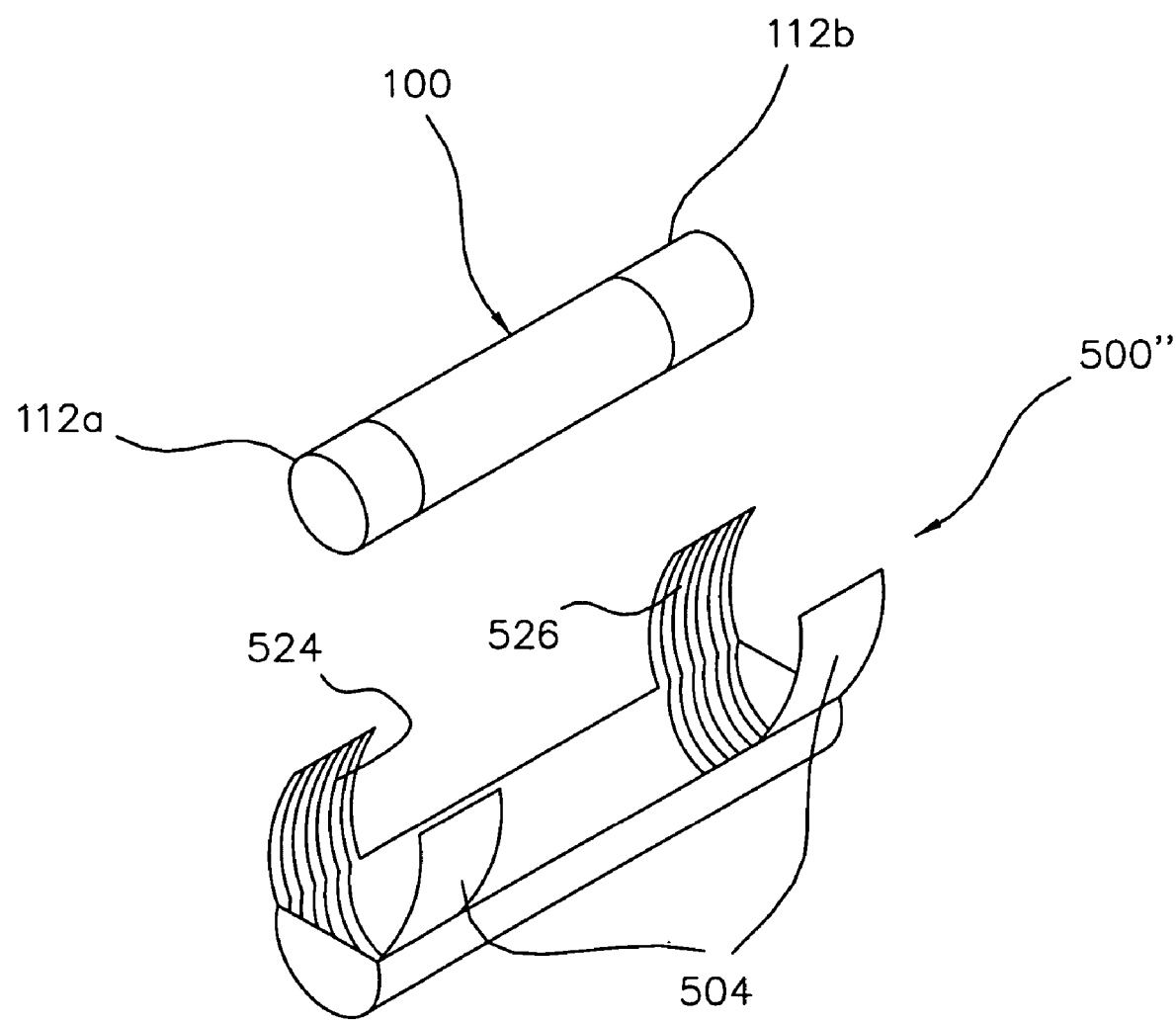
FIG. 33 is an alternative embodiment of the placement structure of FIG. 25 wherein inner portions of the wings and the cavity include conductive layers (preferably a plurality of conductive paths) to provide additional electrical coupling between the electrodes of the implantable device axially along the neural/muscular tissue.
Figure 34:
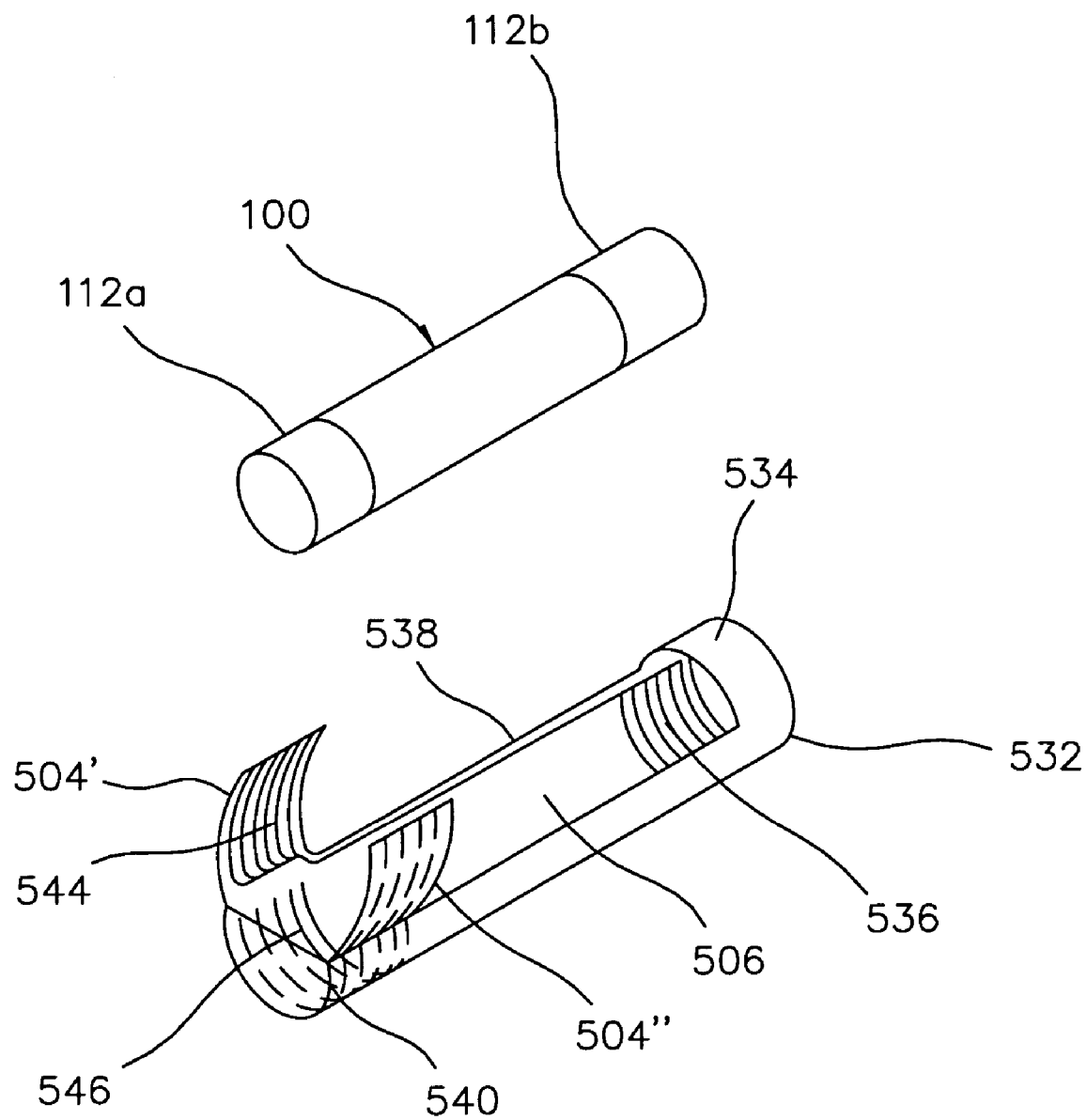
FIG. 34 is a next alternative embodiment of the placement structure of FIG. 25 wherein inner portions of the wings and the cavity include conductive layers (preferably a plurality of conductive paths) to provide additional electrical coupling between the electrodes of the implantable device transversely across the neural/muscular tissue using a pair of wings.

While a cut-down procedure may be used, it is preferred that implantable device 100 within the placement structure 500 be inserted with a hypodermic type insertion tool, e.g., an adapted laparoscopic device 516 (see FIG. 30 and U.S. Pat. No. 6,582,441 which is incorporated herein by reference). In preparation for implantation, the wings 504 of the placement structure 500 are preferably folded inward in proximity to the implantable device 100 within holder 502 and the combination is inserted within the laparoscopic device 516 (see FIG. 31). The laparoscopic device 516 is then inserted as is known in the art into the patient until the tip 518 of laparoscopic device 516 approaches the desired insertion point of the neural/muscular tissue. Upon reaching its desired insertion point, the placement structure 500 is ejected from the laparoscopic device 516 (or conversely and equivalently, the laparoscopic device 516 is withdrawn while the placement structure 500 is held at the desired insertion point) and the wings 504 elastically extend to their nominal position (see FIG. 28) where they are suitable for capturing the neural/muscular tissue 512.

In a first preferred embodiment 500' (see FIG. 27), the electrodes 112 of the implantable device 100 directly make contact with the neural/muscular tissue 512 at electrode/tissue contact points 520 and 522 (for the exemplary two electrode implantable device 100). Accordingly, the initial depolarization (or sensing) associated with the implantable device 100 extends axially along the neural/muscular tissue 512.

In a second preferred embodiment 500" (see FIG. 33), the wings 504 and a portion of the cavity 506 include conductive layers 524, 526 (preferably comprised of a plurality of discrete conductive paths, e.g., comb shaped, slotted, or formed of serpentine paths, to reduce eddy currents and heat build up associated with the receipt of RF fields during charging). Accordingly (again referring to FIG. 32), the conductive layer 524 now additionally makes contact with at contact surfaces 528 and 530 (in addition to contact point 520) and thus there are now three contact point areas associated with each electrode 112 and thus current flow within the neural/muscular tissue 512 may be increased without increasing the compliance voltage since there will now be a lower resistance between the electrodes 112 and the neural/muscular tissue 512.

In a third preferred embodiment 500''' (see FIG. 34), the initial depolarization (or sensing) is applied transversely to the neural/muscular tissue 512 through a single pair of wings 504. In this embodiment, the distal end 532 of the capture device 500''' is a boot type structure 534 that is suitable for capturing distal electrode 112b of the implantable device 100. Within the boot type structure 534, a conductive layer 536 (preferably a plurality of paths, e.g., slotted, to reduce eddy circuits, as previously described) electrically connect the distal electrode 112b of the implantable device 100 along pathway 538 to first proximal wing 504' at the proximal end 540 of the capture device 500'''. Preferably, wing 504' is longer/wider than the proximal electrode 112a so that electrical pathway 538 and its associated conductive layers 536 and 542 do not make contact with the proximal electrode 112a. Conductive layer 546 extends from within the cavity 506 at the proximal end 540 to the inner surface of second proximal wing 504". Accordingly, once inserted, the distal electrode 112b is electrically coupled to first proximal wing 504' and the proximal electrode 112a is electrically coupled to the second proximal wing 504". Once the placement structure 500''' is used to capture the neural/muscular tissue 512, stimulation vectors 548 and 550 are applied transversely to the tissue 512 (see FIG. 32). Alternatively, the electrical pathways associated with second proximal wing 504" may be omitted, in which case only stimulation vector 550 is present. (Note, the polarity of the stimulation vector is only shown for exemplary purposes and may be reversed as needed. Furthermore, the use of the term stimulation vector is equally applicable to describe the vector for sensing a neural/muscular signal, i.e., a sensor or stimulation/sensor vector.)

In the third preferred embodiment 500''', the implantable device 100 is inserted into the capture device 500''' by first inserting the distal end, i.e., electrode 112b, of the implantable device 100 into the boot type structure 534 of the placement structure 500''' and then pressing the proximal end, i.e., electrode 112a, of the implantable device 100 into the proximal end 540 of the placement structure 500'''. This differs from the other two embodiments where both ends of the implantable device 100 are preferably inserted concurrently into the placement structure.

Notably, in the third preferred embodiment, there is only one set of wings, i.e., first and second proximal wings 504' and 504". Accordingly, during implantation, only a single pair of wings need to capture the neural/muscular tissue 512 and thus implantation is simplified.

FIG. 35 is an alternative embodiment 500''' of the placement structure of FIG. 25 and the implantable medical device of FIGS. 1A–10D wherein the implantable medical device 100" additionally includes a plurality of stimulator/sensor circuitry portions 560 (e.g., 560a–560n) that are coupled to inner portions of the wings 504 via electrode connectors 562, 564 on the outer surface of the implantable medical device 100" and the cavity of the placement structure 500''' includes a plurality of conductive paths to provide electrical coupling between the electrode connectors 562, 564 of the implantable device 100" to electrodes 567, 569 within the wings 504 for coupling to displaced portions of the neural/muscular tissue. In this embodiment, the implantable medical device 100" includes a plurality of stimulator/sensor circuitry portions 560 each of which includes the capabilities of the aforementioned stimulator circuitry 110 and/or sensor circuitry 188 described in reference to FIG. 3A. Accordingly, when used with a plurality of stimulator circuitry portions 560, each portion may be stimulated with different current intensities and/or timing and thereby steer the stimulation pulses to a desired portion (foci) of the neural/muscular tissue. Alternatively or additionally, a plurality of sensor circuitry portions 560 may be used to sense neural/muscular responses from different portions of the neural/muscular tissue, e.g., to sense evoked responses or discrete neural/muscular signals.

FIG. 35 is an alternative embodiment 500''' of the placement structure of FIG. 25 and the implantable medical device of FIGS. 10A–10D wherein the implantable medical device 100" additionally includes a plurality of stimulator/sensor circuitry portions 560 (e.g., 560a–560n) that are coupled to inner portions of the wings 504 via electrode connectors 562, 564 on the outer surface of the implantable medical device 100" and the cavity of the placement structure 500''' includes a plurality of conductive paths to provide electrical coupling between the electrode connectors 562, 564 of the implantable device 100" to electrodes 567, 569 within the wings 504 for coupling to displaced portions of the neural/muscular tissue. In this embodiment, the implantable medical device 100" includes a plurality of stimulator/sensor circuitry portions 560 each of which includes the capabilities of the aforementioned stimulator circuitry 110 and/or sensor circuitry 188 described in reference to FIG. 3A. Accordingly, when used with a plurality of stimulator circuitry portions 560, each portion may be stimulated with different current intensities and/or timing and thereby steer the stimulation pulses to a desired portion (foci) of the neural/muscular tissue. Alternatively or additionally, a plurality of sensor circuitry portions 560 may be used to sense neural/muscular responses from different portions of the neural/muscular tissue, e.g., to sense evoked responses or discrete neural/muscular signals.

FIG. 36 shows an alternative implementation of that which was functionally described in relation to FIG. 35. However, in this implementation a single, essentially U-shaped, structure 600 having elastic wings 504 is integrally formed which encompasses the functionality of the implantable medical device 100" contained within the placement structure 500'". In this single integral structure 600, a plurality of electrodes 602, 604, 606 (e.g., 602a–602n, 604a–604n, 606a–606n) are distributed (and preferably individually driven by circuitry portions 560 contained within the U-shaped structure 600 along with other circuitry as described in reference to FIG. 3A) within the inner U-shaped cavity 608 of structure 600.

FIG. 37 shows a next alternative implementation of an integral device 650 similar to that shown in FIG. 36 to the extent that it too is an integral device but in this case it has its elastic wings 504 formed from a silicon rubber impregnated cloth that is permanently attached to the functional equivalent of the implantable medical device 100" described in reference to FIG. 35. In most other aspects, this embodiment is functionally equivalent to that which has been previously described.

Figures 28, 29:
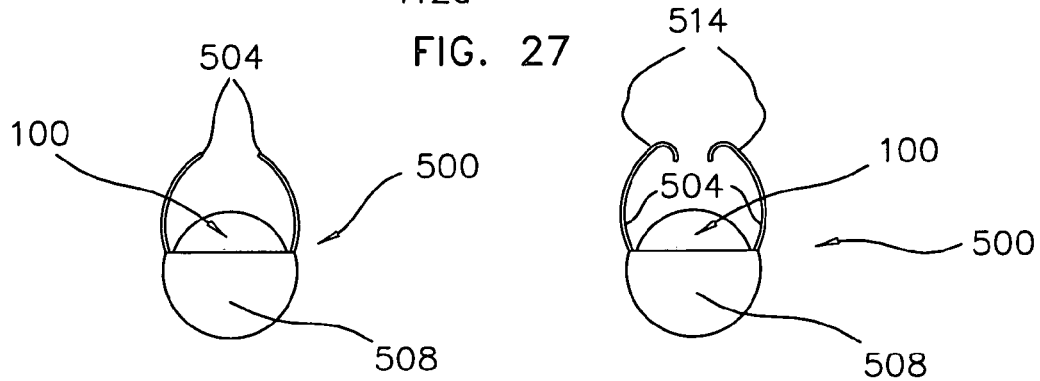
FIG. 28 is an end view of the placement structure of FIGS. 25 and 26.
FIG. 29 is an end view of the placement structure of FIGS. 25 and 26 having hooks at the ends of its wings for providing additional means for retaining the placement structure in close proximity to the neural/muscular tissue.
Figure 31:
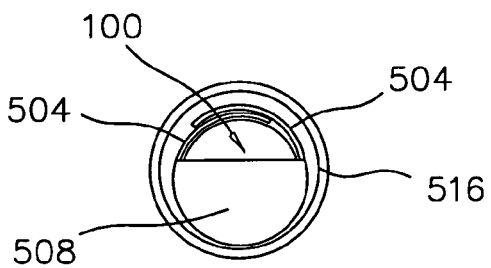
FIG. 31 is a cross sectional view of that shown in FIG. 30 along the line 31—31 wherein the wings of the placement structure have been folded inward toward the implantable device before insertion, e.g., via its tip, into the hollow portion of the laparoscopic device.

While the invention herein disclosed has been described by means of specific embodiments and applications thereof, numerous modifications and variations could be made thereto by those skilled in the art without departing from the scope of the invention. For example, while not expressly shown, the hook portions shown and described in reference to FIG. 29 are equally applicable to the embodiments of FIGS. 36 and 37. It is therefore to be understood that within the scope of the claims, the invention may be practiced otherwise than as specifically described herein.

What is claimed is:

1. A system configured for stimulating tissue internal to a patient's body, said system comprising:
    at least one sealed elongate housing having a non-circular cross section and configured for implantation via injection in said patient's body, said housing having axial and lateral dimensions selected from the group consisting of:
        (a) an axial dimension of less than 60 mm and a lateral dimension of greater than or equal to 6 mm;
        (b) an axial dimension of greater than 60 mm and a lateral dimension of less than or equal to 6 mm; and
        (c) an axial dimension of less than or equal to 60 mm and a lateral dimension of less than or equal to 6 mm;
    power consuming circuitry carried by said housing including at least one electrode extending externally of said housing, said power consuming circuitry including a capacitor and pulse control circuitry for controlling (1) the charging of said capacitor and (2) the discharging of said capacitor to produce a current pulse through said electrode;
    a battery disposed in said housing electrically connected to said power consuming circuitry for powering said pulse control circuitry and charging said capacitor, said battery having a capacity of at least one microwatt-hour;
    an internal coil and a charging circuit disposed in said housing for supplying a charging current to said battery;
    an external coil adapted to be mounted outside of said patient's body; and
    means for energizing said external coil to generate an alternating magnetic field for supplying energy to said charging circuit via said internal coil.

2. The system of claim 1 wherein said non-circular cross section is selected from the group consisting of:
    (a) rectangular;
    (b) triangular;
    (c) oval;
    (d) hexagonal;
    (a) octagonal; and
    (f) polygon shaped.

3. The system of claim 1 wherein said power consuming circuitry further includes:
    a controller coupled to said pulse control circuitry and responsive to stored configuration data for defining the characteristics of said current pulse; and
    a data signal receiver responsive to a command signal for modifying said stored configuration data.

4. The system of claim 2 further including a sensor in said housing for detecting a static magnetic field; and wherein
    said sensor is coupled to said controller for modifying said current pulse produced in said externally extending electrode.

5. The system of claim 2 further including a command signal generator; and
    wireless communication means for coupling said command signal generator to said data signal receiver.

6. The system of claim 2 wherein said power consuming circuitry further includes a data signal transmitter for transmitting a data signal.

7. The system of claim 1 wherein said controller is selectively operable to (1) produce a sequence of drive pulses through said externally extending electrode, (2) monitor an electrical signal from said externally extending electrode, and/or (3) cause said data signal transmitter to transmit a data signal related to said command signal received by said data signal receiver.

8. The system of claim 1 further including means for causing said transmitter to transmit a data signal related to said command signal received by said data signal receiver.

9. A system for monitoring and/or affecting at least one parameter of a patient's body, said system comprising:
    at least one implantable device operable to sense and/or stimulate a patient's body parameter in accordance with one or more controllable operating parameters; and
    a system control unit for controlling said controllable operating parameters, said system control unit comprising:
        a sealed elongate housing having a non-circular cross section and suitable for implantation via injection into a patient's body, said housing having axial and lateral dimensions selected from the group consisting of:
            (a) an axial dimension of less than 60 mm and a lateral dimension of greater than or equal to 6 mm;
            (b) an axial dimension of greater than 60 mm and a lateral dimension of less than or equal to 6 mm; and
            (a) an axial dimension of less than or equal to 60 mm and a lateral dimension of less than or equal to 6 mm;

a signal transmitter in said housing for transmitting command signals;

a signal receiver in said housing for receiving status signals; and a programmable controller in said housing responsive to received status signals for producing command signals for transmission by said signal transmitter to said implantable devices.

10. The system of claim 9 wherein said non-circular cross section is selected from the group consisting of:
(a) rectangular;
(b) triangular;
(c) oval;
(d) hexagonal;
(e) octagonal; and
(f) polygon shaped.

11. The system of claim 9 comprising at least one said implantable device operable as a sensor and at least one said implantable device operable as a stimulator and wherein said controller is responsive to status data signals received from said sensor for generating said addressable command data signals to said stimulator to perform closed loop control of the operation of said stimulator.

12. The system of claim 9 wherein said system control unit additionally comprises a power source contained within said sealed housing for providing operating power to said data signal transmitter, said data signal receiver, and said programmable controller.

13. The system of claim 9 wherein said system control unit additionally includes:
at least one electrode;
sensor/stimulator circuitry; and wherein
said sensor stimulator circuitry is configurable to generate a data signal representative of an electrical signal conducted by said electrode and/or supply a sequence of drive pulses to said electrode.

14. The system of claim 9 wherein each of said implantable devices includes a power source having a capacity of at least 1 microwatt-hour.

15. The system of claim 14 wherein each said implantable device includes means for monitoring status of its power source and said system control unit is configured to transmit command signals to each said implantable device and to responsively receive status signals corresponding to said power source status.

16. The system of claim 9 further including:
program storage means in said housing for specifying the operation of said programmable controller; and
means to modify said program storage means in response to signals received by said signal receiver.

17. The system of claim 16 wherein said program storage means includes means to cause said system control unit to transmit a programmable list of command signals to said implantable devices.

18. The system of claim 17 wherein said means to cause said system control unit to transmit a programmable list of command signals includes:
a magnetic sensor for generating a signal responsive to a DC magnetic field; and wherein
said programmable list of command signals is transmitted in response to said magnetic sensor signal.

19. A system control unit configured for controlling and monitoring the operation of one or more other implantable addressable controllable devices wherein each of said controllable devices is contained within a sealed elongate housing suitable for injection into a patient's body and having a non-circular cross section selected from the group consisting of: (a) an axial dimension of less than 60 mm and a lateral dimension of greater than or equal to 6 mm, (b) an axial dimension of greater than 60 mm and a lateral dimension of less than or equal to 6 mm, and (c) an axial dimension of less than or equal to 60 mm and a lateral dimension of less than or equal to 6 mm, and wherein at least one of said devices is configurable to modify at least one parameter of the patient's body, said system control unit comprising:
a control unit housing;
a data signal transmitter for wireless transmission of command data signals to selectively addressed controllable devices;
a data signal receiver for wireless reception of status data signals from selectively addressed controllable devices;
a controller capable of accepting status data signals from said data signal receiver and sending addressable command data signals to said data signal transmitter in response thereto to selectively control or monitor the operation of one or more of said selectively addressed controllable devices in a closed loop manner in accordance with one or more controllable operating parameters for modifying at least one parameter of the patient's body;
program storage for specifying the operation of said controller; and wherein said data signal transmitter, data signal receiver, said controller, and said program storage are disposed within said control unit housing.

20. The system control unit of claim 19 wherein said control unit housing is sealed and suitable for implantation via injection into a patient's body and has axial and lateral dimensions selected from the group consisting of:
(a) an axial dimension of less than 60 mm and a lateral dimension of greater than or equal to 6 mm;
(b) an axial dimension of greater than 60 mm and a lateral dimension of less than or equal to 6 mm; and
(c) an axial dimension of less than or equal to 60 mm and a lateral dimension of less than or equal to 6 mm.

21. The system control unit of claim 19 additionally comprising a power source contained within said control unit housing for providing operating power to said data signal transmitter, said data signal receiver, said controller, and said program storage.

22. The system control unit of claim 19 wherein said program storage is modified in response to signals received by said data signal receiver.

23. The system control unit of claim 19 additionally including:
at least one electrode;
sensor circuitry; and wherein
said sensor circuitry is configurable to generate a data signal representative of an electrical signal conducted by said electrode.

24. The system control unit of claim 19 additionally including:
at least one electrode;
stimulator circuitry; and wherein
said stimulator circuitry is configurable to supply a sequence of drives pulses to said at least one electrode.

25. The system control unit of claim 24 wherein said supplied sequence of drive pulses is altered in response to a status signal received from at least one of said implantable addressable controllable devices.

26. The system control unit of claim 19 wherein at least one of said implantable addressable controllable devices operates as a stimulator and includes at least one electrode and stimulator circuitry for delivering a sequence of drive pulses to said at least one electrode and said system control unit periodically transmits a command signal to said stimulator in response to a status signal received from another one of said implantable addressable controllable devices.

27. The system control unit of claim 19 additionally comprising a rechargeable battery for powering said system control unit.

28. The system control unit of claim 27 wherein said battery has a capacity of at least one watt hour.

29. The system control unit of claim 19 wherein each of said implantable addressable controllable devices includes a rechargeable battery for powering each said implantable addressable controllable device.

30. The system control unit of claim 29 wherein said battery for each of said implantable addressable devices has a capacity of at least one microwatt-hour.

31. The system control unit of claim 19 wherein said system control unit is configured for implantation in the patient's body.

32. The system control unit of claim 19 wherein said system control unit is configured for use outside of the patient's body.

33. A system control unit configured for controlling and monitoring the operation of one or more other implantable addressable controllable devices wherein each of said controllable devices is contained within a sealed elongate housing suitable for injection into a patient's body and having a non-circular cross section selected from the group consisting of: (a) an axial dimension of less than 60 mm and a lateral dimension of greater than or equal to 6 mm, (b) an axial dimension of greater than 60 mm and a lateral dimension of less than or equal to 6 mm, and (c) an axial dimension of less than or equal to 60 mm and a lateral dimension of less than or equal to 6 mm, and wherein at least one of said devices is configurable as a stimulator to modify at least one parameter of the patient's body and at least one of said devices is configurable as a sensor to sense at least one parameter of the patient's body, said system control unit comprising:
  a control unit housing;
  a data signal transmitter for wireless transmission of command data signals to selectively addressed controllable devices;
  a data signal receiver for wireless reception of status data signals from selectively addressed controllable devices;
  a controller capable of accepting status data signals from said data signal receiver from one or more of said selectively addressed controllable devices operating as sensors and sending addressable command data signals to said data signal transmitter in response thereto to selectively control the operation of one or more of said selectively addressed controllable devices operating as stimulators to thereby operate in a closed loop manner for modifying at least one parameter of the patient's body;
  program storage for specifying the operation of said controller; and wherein
  said data signal transmitter, data signal receiver, said controller, and said program storage are disposed within said control unit housing.

34. The system control unit of claim 33 wherein said system control unit is configured for implantation in the patient's body.

35. The system control unit of claim 33 wherein said system control unit is configured for use outside of the patient's body.

36. A system for monitoring and/or affecting at least one parameter of a patient's body comprised of a system control unit capable of wireless communication with one or more implantable devices suitable for implantation within the patient's body, wherein each of said implantable devices is contained with a sealed elongate housing having a non-circular cross section and includes a power source having a power capacity of at least 1 microwatt-hour, said housing having an axial and lateral dimensions selected from the group consisting of:
  (a) an axial dimension of less than 60 mm and a lateral dimension of greater than or equal to 6 mm;
  (b) an axial dimension of greater than 60 mm and a lateral dimension of less than or equal to 6 mm; and
  (c) an axial dimension of less than or equal to 60 mm and a lateral dimension of less than or equal to 6 mm.

37. A device suitable for implantation via injection beneath the skin of a patient's body, said device comprising:
  a sealed elongate housing having an axial dimension of less than 60 mm and a lateral dimension of less than 6 mm;
  power consuming circuitry carried by said housing having at least one electrode extending externally of said housing for tissue stimulation and/or body parameter monitoring, wherein said power consuming circuitry includes communication circuitry for accepting remotely provided command messages to thereby modify operation of said device;
  a battery disposed in said housing electrically connected to said power consuming circuitry for powering said circuitry; and wherein
  said battery has an energy capacity of at least 1 microwatt-hour.

38. The device of claim 37 wherein said power source comprises a battery including:
  a case;
  a first conductive plate mounted in said case;
  a second conductive plate mounted in said case in opposed spaced relationship relative to said first plate;
  an electrolyte disposed between said first and second plates; and wherein
  said plates are formed to include gaps to accordingly minimize eddy currents therein.

39. The device of claim 37 wherein said battery is rechargeable, said device further comprising an internal coil and a charging circuit disposed in said housing for supplying a charging current to said rechargeable battery in response to an externally provided AC magnetic field.

40. The device of claim 37 wherein said battery is a primary battery.

41. The device of claim 37 wherein said power consuming circuitry includes:
  a controller;
  address storage means for storing an identification address;
  input/output driver circuitry coupled to said at feast one electrode; and wherein
  said communication circuitry includes a data signal receiver for receiving a command message identifying said stored address for selectively actuating said input/output driver circuitry.

42. The device of claim 41 wherein said data signal receiver includes a coil responsive to a command message defined by a modulated magnetic field.

43. The device of claim 41 wherein said data signal receiver includes a transducer responsive to a command message defined by a modulated ultrasonic signal.

44. The device of claim 41 wherein said communication circuitry further includes a data signal transmitter for remotely transmitting a data signal and thereby providing a bidirectional communication capability with an external device.

45. The device of claim 41 wherein said input/output driver circuitry coupled to at least one electrode is configured to produce an electrical current for stimulating tissue; and wherein
said controller supplies a sequence of drive pulses to said electrode when said input/output driver circuitry is actuated.

46. The device of claim 45 further including:
a sensor coupled to said controller responsive to a static magnetic field; and wherein
said controller is configured to modify the function of said device in response to a static magnetic field detected by said sensor.

47. The device of claim 44 wherein said device is configurable via a command data signal identifying said stored address to selectively operate to (1) supply a sequence of drive pulses to said at least one electrode via said input/output driver circuitry, and/or (2) monitor an electrical signal from said at least one electrode via said input/output driver circuitry.

* * * * *